US007727987B2

(12) United States Patent
Moser et al.

(10) Patent No.: US 7,727,987 B2
(45) Date of Patent: Jun. 1, 2010

(54) CRYSTALLINE FORMS OF (6R)-L-ERYTHRO-TETRAHYDROBIOPTERIN DIHYDROCHLORIDE

(75) Inventors: Rudolf Moser, Schaffhausen (CH); Viola Groehn, Dachsen (CH); Thomas Egger, Kempthal (CH); Fritz Blatter, Reinach (CH)

(73) Assignee: Merck Eprova AG, Schaffhausen (CH)

( * ) Notice: Subject to any disclaimer, the term of this patent is extended or adjusted under 35 U.S.C. 154(b) by 331 days.

(21) Appl. No.: 10/990,316

(22) Filed: Nov. 17, 2004

(65) Prior Publication Data

US 2006/0035900 A1 Feb. 16, 2006

Related U.S. Application Data

(60) Provisional application No. 60/520,377, filed on Nov. 17, 2003.

(51) Int. Cl.
*A61K 31/221* (2006.01)
*C07D 475/04* (2006.01)
*A61P 25/16* (2006.01)

(52) U.S. Cl. ...................................... 514/249; 544/258

(58) Field of Classification Search ................ 544/258; 514/249

See application file for complete search history.

(56) References Cited

U.S. PATENT DOCUMENTS 4,595,752 A * 6/1986 Azuma et al. ............... 544/258
4,758,571 A * 7/1988 Curtius et al. ............... 514/249
6,544,994 B2 * 4/2003 Rabelink et al. ............ 514/249

FOREIGN PATENT DOCUMENTS

EP 0 191 335 8/1986
WO WO 2005/065018 A2 7/2005

OTHER PUBLICATIONS

Arnold, Phenylketonuria, eMedicine from webMD, Jun. 5, 2006, http://www.emedicine.com/PED/topic1787.htm.*

Schircks Laboratories, Tetrahydrobiopterin, Sales restrictions, Jun. 2006, http://www.schircks.com/tablets/tablet_info.htm.*

Disorders Index of the National Institute of Neurological Disorders and Stroke, Oct. 2006 http://www.ninds.nih.gov/disorders/disorder_index.htm?css=print.*

Choi, et al., Tetrahydrobiopterin is Released from and Causes Preferential Death of Catecholaminergic Cells by Oxidative Stress, Molecular Pharmacology, vol. 58, No. 3, 2000, 633-640.*

Galley, et al., Brit. J. Anaesthesia, 86(4): 578-80 (2001).*

Tsai, et al., Psychosomatic Medicine 61:651-665 (1999).*

Smith, MedPage Today, Apr. 20, 2007.*

Khripak, et al., Khimiya Geterotsiklicheskikh Soedinenii, No. 6, pp. 844-846, Jun. 1975.*

Schisla, et al., Zeolites, vol. 16, No. 2, Feb. 1996, pp. 221.*

U.S. Appl. No. 60/520,767, Daniel Oppenheimer, filed Nov. 17, 2003.

U.S. Appl. No. 10/991,573, Daniel Oppenheimer, filed Nov. 17, 2004.

U.S. Appl. No. 11/143,887, Daniel Oppenheimer, filed Jun. 1, 2005.

U.S. Patent Publication No. 20060035900A1, published Feb. 16, 2006.

U.S. Appl. No. 11/542,310, Daniel Oppenheimer, filed Oct. 2, 2006.

Statement For The Record filed Feb. 25, 2008.

J. Biochem. 98, 1341-1348 (1985)—vol. 98, No. 5, 1985—Stereochemistry of Biopterin Cofactor and Facile Methods for the Determination of the Stereochemistry of a Biologically Active 5,6,7,8-Tetrahydropterin[1,2,3], Sadao Matsuura et al.

Heterocycles, vol. 23, No. 12, 1985—pp. 3115-3120—Hydrogenation of Biopterin and Its Analogues; Application For The Convenient Procedure of Biopterin Cofactor and Related 5,8,7,8-Tetrahydropterins—Sadao Matsuura et al.

Chemistry Letters, pp. 735-738, 1984—The Chemical Society of Japan 1984—pp. 735-738—Highly Stereoselective Procedure for (6R)-Tetrahydrobiopterin Cofactor—Sadao Matsuura et al.

Schircks Laboratories—Tetrahydrobiopterin Tablets, Jan. 8, 2008.

* cited by examiner

*Primary Examiner*—James O Wilson
*Assistant Examiner*—Cecilia M Jaisle
(74) *Attorney, Agent, or Firm*—Millen, White, Zelano & Branigan, P.C.

(57) ABSTRACT

Crystal forms of (6R)-L-erythro-tetrahydrobiopterin dihydrochloride, hydrates and solvates and processes for their preparation are provided. These crystal forms are either intermediates for the preparation of stable polymorphic form B or are suitable for solid formulations.

20 Claims, 15 Drawing Sheets

Powder X-ray Diffraction Pattern of (6R)-L-erythro-Tetrahydrobiopterin Dihydrochloride Form A
I1188-01: NPF93-P10
counts
1000
900
800
700
600
500
400
300
200
100
0
0
5
10
15
20
25
30
35
40
2 theta angle Powder X-ray Diffraction Pattern of (6R)-L-erythro-Tetrahydrobiopterin Dihydrochloride Form B
I1170-01: NPF93-P1
counts
4500
4000
3500
3000
2500
2000
1500
1000
500
0
0
5
10
15
20
25
30
35
40
2 theta angle Powder X-ray Diffraction Pattern of (6R)-L-erythro-Tetrahydrobiopterin Dihydrochlorid Form C
I1245-01: NPF93-P22
counts/s
1500
1250
1000
750
500
250
0
0
5
10
15
20
25
30
35
40
2 theta angle Powder X-ray Diffraction Pattern of (6R)-L-erythro-Tetrahydrobiopterin Dihydrochlorid Form D
K0304-01: NPF93-P68
counts/s
5000
4500
4000
3500
3000
2500
2000
1500
1000
500
0
0
5
10
15
20
25
30
35
40
2 theta angle Powder X-ray Diffraction Pattern of (6R)-L-erythro-Tetrahydrobiopterin Dihydrochloride Form E
CLZ-04: NPF93-P50
counts/s
0
500
1000
1500
2000
2500
3000
3500
2 theta angle
0
5
10
15
20
25
30
35
40

Powder X-ray Diffraction Pattern of (6R)-L-erythro-Tetrahydrobiopterin Dihydrochloride Form F

Powder X-ray Diffraction Pattern of (6R)-L-erythro-Tetrahydrobiopterin Dihydrochloride Form G

Powder X-ray Diffraction Pattern of (6R)-L-erythro-Tetrahydrobiopterin Dihydrochloride Form H
I1242-01: NPF93-P25
counts/s
5000
4500
4000
3500
3000
2500
2000
1500
1000
500
0
0
5
10
15
20
25
30
35
40
2 theta angle Powder X-ray Diffraction Pattern of (6R)-L-erythro-Tetrahydrobiopterin Dihydrochloride Form I
K0317-01: NPF93-P73
counts/s
4500
4000
3500
3000
2500
2000
1500
1000
500
0
5
10
15
20
25
30
35
40
2 theta angle Powder X-ray Diffraction Pattern of (6R)-L-erythro-Tetrahydrobiopterin Dihydrochloride Form J
K0387-01: NPF93-P89
counts/s
3000
2500
2000
1500
1000
500
0
0
5
10
15
20
25
30
35
40
2 theta angle Powder X-ray Diffraction Pattern of (6R)-L-erythro-Tetrahydrobiopterin Dihydrochloride Form L
X03540T- T8 Merck Eprova (P51)
counts/s
0
500
1000
1500
2000
2500
3000
3500
4000
4500
0
5
10
15
20
25
30
35
40
2 theta angle Powder X-ray Diffraction Pattern of (6R)-L-erythro-Tetrahydrobiopterin Dihydrochloride Form M
CPT-01: NPF93-P86
counts/s
2 theta angle
0
100
200
300
400
500
600
700
800
900
1000
0
5
10
15
20
25
30
35
40

CRYSTALLINE FORMS OF (6R)-L-ERYTHRO-TETRAHYDROBIOPTERIN DIHYDROCHLORIDE

This application claims the benefit of the filing date of U.S. Provisional Application Ser. No. 60/520,377 filed Nov. 17, 2003 which is incorporated by reference herein.

The present invention relates to crystal forms of (6R)-L-erythro-tetrahydrobiopterin dihydrochloride and hydrates and solvates thereof. This invention also relates to processes for preparing the crystal forms of (6R)-L-erythro-tetrahydrobiopterin dihydrochloride and hydrates and solvates thereof. This invention also relates to compositions comprising selected and stable crystal forms of (6R)-L-erythro-tetrahydrobiopterin dihydrochloride or a hydrate thereof and a pharmaceutically acceptable carrier.

It is known that the biosynthesis of the neurotransmitting catecholamines from phenylalanine requires tetrahydrobiopterin cofactor, (6R)-2-amino-4-oxo-6-[(1R,2S)-1,2-dihydroxypropyl]-5,6,7,8-tetrahydropteridine according to formula (I), (I)

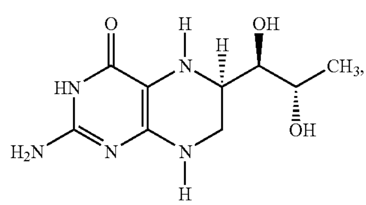

at the monooxygenation step of phenylalanine and tyrosine. It is supposed that the catecholamine biosynthesis is regulated in a great extent by tetrahydrobiopterin cofactor, and that a decrease of the cofactor in central nerve systems causes several neurological disorders such as parkinsonism and atypical phenylketonuria. The compound of formula I is therefore an effective therapeutic agent for treatment of said disorders in mammals in need thereof.

The compound of formula I is difficult to handle and it is therefore produced and offered as its dihydrochloride salt (Schircks Laboratories, CH-8645 Jona, Switzerland) even in ampoules sealed under nitrogen to prevent degradation of the substance due to its hygroscopic nature and sensitivity to oxidation. U.S. Pat. No. 4,649,197 discloses that separation of (6R)- and 6(S)L-erythro-tetrahydrobiopterin dihydrochloride into its diastereomers is difficult due to the poor crystallinity of 6(R,S)-L-erythro-tetrahydrobiopterin dihydrochloride. In EP-A1-0 079 574 is described the preparation of tetrahydrobiopterin, where a solid tetrahydrobiopterin dihydrochloride is obtained as an intermediate. S. Matsuura et al. describes in Chemistry Letters 1984, pages 735-738 and Heterocycles, Vol. 23, No. 12, 1985 pages 3115-3120 6(R)-tetrahydrobiopterin dihydrochloride as a crystalline solid in form of colourless needles, which are characterized by X-ray analysis disclosed in J. Biochem. 98, 1341-1348 (1985). An optical rotation of 6.81° was found the crystalline product, which is quite similar to the optical rotation of 6.51° reported for a crystalline solid in form of white crystals in example 6 of EP-A2-0 191 335.

Results obtained during investigation and development of (6R)-L-erythro-tetrahydrobiopterin dihydrochloride development revealed that the known crystalline solids can be designated as form B, for which was found a characteristic X-ray powder diffraction pattern with characteristic peaks expressed in d-values (Å):

8.7 (vs), 6.9 (w), 5.90 (vw), 5.63 (m), 5.07 (m), 4.76 (m), 4.40 (m), 4.15 (w), 4.00 (s), 3.95 (m), 3.52 (m), 3.44 (w), 3.32 (m), 3.23 (s), 3.17 (w), 3.11 (vs), 3.06 (w), 2.99 (w), 2.96 (w), 2.94 (m), 2.87 (w), 2.84 (s), 2.82 (m), 2.69 (w), 2.59 (w), 2.44 (w). A characteristic X-ray powder diffraction pattern is exhibited in FIG. 2.

Here and in the following the abbreviations in brackets mean: (vs)=very strong intensity; (s)=strong intensity; (m)=medium intensity; (w)=weak intensity; and (vw)=very weak intensity.

Polymorph B is a slightly hygroscopic anhydrate with the highest thermodynamic stability above about 20° C. Furthermore, form B can be easily processed and handled due to its thermal stability, possibility for preparation by targeted conditions, its suitable morphology and particle size. Melting point is near 260° C. ($\Delta H_f$>140 J/g), but no clear melting point can be detected due to decomposition prior and during melting. These outstanding properties renders polymorph form B especially feasible for pharmaceutical application, which are prepared at elevated temperatures. Polymorph B can be obtained as a fine powder with a particle size that may range from 0.2 μm to 500 μm.

However, there is a need for other stable forms of (6R)-L-erythro-tetrahydrobiopterin dihydrochloride with satisfactory chemical and physical stability for a safe handling during manufacture and formulation as well as providing a high storage stability in its pure form or in formulations. In addition, there is a strong need for processes to produce polymorph B and other crystalline forms of (6R)-L-erythro-tetrahydrobiopterin dihydrochloride on a large scale in a controlled manner Results obtained during development of (6R)-L-erythro-tetrahydrobiopterin dihydrochloride indicated that the compound may exist in different crystalline forms, including polymorphic forms and solvates. The continued interest in this area requires an efficient and reliable method for the preparation of the individual crystal forms of (6R)-L-erythro-tetrahydrobiopterin dihydrochloride and controlled crystallization conditions to provide crystal forms, that are preferably stable and easy to handle and to process in the manufacture and preparation of formulations, and that provide a high storage stability in substance form or as formulated product, or which provide less stable forms suitable as intermediates for controlled crystallisation for the manufacture of stable forms.

1. Polymorphic Forms of (6R)-L-erythro-tetrahydrobiopterin dihydrochloride

Polymorphic forms A, B, F, J and K are anhydrates, which absorb up to about 3% by weight of water when exposed to open air humidity at ambient temperature.

A first object of the invention is crystalline polymorph of (6R)-L-erythro-tetrahydrobiopterin dihydrochloride, which exhibits a characteristic X-ray powder diffraction pattern with characteristic peaks expressed in d-values (Å):

15.5 (vs), 12.0 (m), 4.89 (m), 3.70 (s), 3.33 (s), 3.26 (s), and 3.18 (m);

hereinafter designated as form A.

In a more preferred embodiment, the present invention comprises a crystalline polymorph of (6R)-L-erythro-tetrahydrobiopterin dihydrochloride, which exhibits a characteristic X-ray powder diffraction pattern with characteristic peaks expressed in d-values (Å):

15.5 (vs), 12.0 (m), 6.7 (m), 6.5 (m), 6.3 (w), 6.1 (w), 5.96 (w), 5.49 (m), 4.89 (m), 3.79 (m), 3.70 (s), 3.48 (m), 3.45 (m), 3.33 (s), 3.26 (s), 3.22 (m), 3.18 (m), 3.08 (m), 3.02 (w), 2.95 (w), 2.87 (m), 2.79 (w), 2.70 (w);

hereinafter designated as form A.

In another preferred embodiment, the present invention comprises a crystalline polymorph of (6R)-L-erythro-tetrahydrobiopterin dihydrochloride, which exhibits characteristic Raman bands, expressed in wave numbers ($cm^{-1}$) at:

2934 (w), 2880 (w), 1692 (s), 1683 (m), 1577 (w), 1462 (m), 1360 (w), 1237 (w), 1108 (w), 1005 (vw), 881 (vw), 813 (vw), 717 (m), 687 (m), 673 (m), 659 (m), 550 (w), 530 (w), 492 (m), 371 (m), 258 (w), 207 (w), 101 (s), 87 (s) $cm^{-1}$, hereinafter designated as form A.

In still another preferred embodiment, the present invention comprises a crystalline polymorph A of (6R)-L-erythro-tetrahydrobiopterin dihydrochloride, which exhibits a characteristic X-ray powder diffraction pattern as exhibited in FIG. 1.

The polymorph A is slightly hygroscopic and adsorbs water to a content of about 3 percent by weight, which is continuously released between 50° C. and 200° C., when heated at a rate of 10° C./minute. The polymorph A is a hygroscopic anhydrate which is a meta-stable form with respect to form B; however, it is stable over several months at ambient conditions if kept in a tightly sealed container. Form A is especially suitable as intermediate and starting material to produce stable polymorph forms. Polymorph form A can be prepared as a solid powder with desired medium particle size range which is typically ranging from 1 μm to about 500 μm.

Still another object of the invention is crystalline polymorph of (6R)-L-erythro-tetrahydrobiopterin dihydrochloride, which exhibits a characteristic X-ray powder diffraction pattern with characteristic peaks expressed in d-values (Å):

17.1 (vs), 4.92 (m), 4.68 (m), 3.49 (s), 3.46 (vs), 3.39 (s), 3.21 (m), and 3.19 (m), hereinafter designated as form F.

In a more preferred embodiment, the present invention comprises a crystalline polymorph of (6R)-L-erythro-tetrahydrobiopterin dihydrochloride, which exhibits a characteristic X-ray powder diffraction pattern with characteristic peaks expressed in d-values (Å):

17.1 (vs), 12.1 (w), 8.6 (w), 7.0 (w), 6.5 (w), 6.4 (w), 5.92 (w), 5.72 (w), 5.1.1 (w), 4.92 (m), 4.86 (w), 4.68 (m), 4.41 (w), 4.12 (w), 3.88 (w), 3.83 (w), 3.70 (m), 3.64 (w), 3.55 (m), 3.49 (s), 3.46 (vs), 3.39 (s), 3.33 (m), 3.31 (m), 3.27 (m), 3.21 (m), 3.19 (m), 3.09 (m), 3.02 (m), and 2.96 (m), hereinafter designated as form F.

In still another preferred embodiment, the present invention comprises a crystalline polymorph F of (6R)-L-erythro-tetrahydrobiopterin dihydrochloride, which exhibits a characteristic X-ray powder diffraction pattern as exhibited in FIG. 6.

The polymorph F is slightly hygroscopic and adsorbs water to a content of about 3 percent by weight, which is continuously released between 50° C. and 200° C., when heated at a rate of 10° C./minute. The polymorph F is a meta-stable form and a hygroscopic anhydrate, which is more stable than form A at ambient lower temperatures and less stable than form B at higher temperatures and form F is especially suitable as intermediate and starting material to produce stable polymorph forms. Polymorph form F can be prepared as a solid powder with desired medium particle size range which is typically ranging from 1 μm to about 500 μm.

Still another object of the invention is a crystalline polymorph of (6R)-L-erythro-tetrahydrobiopterin dihydrochloride, which exhibits a characteristic X-ray powder diffraction pattern with characteristic peaks expressed in d-values (Å):

14.6 (m), 3.29 (vs), and 3.21 (vs), hereinafter designated as form J.

In a more preferred embodiment, the present invention comprises a crystalline polymorph of (6R)-L-erythro-tetrahydrobiopterin dihydrochloride, which exhibits a characteristic X-ray powder diffraction pattern with characteristic peaks expressed in d-values (Å):

14.6 (m), 6.6 (w), 6.4 (w), 5.47 (w), 4.84 (w), 3.29 (vs), and 3.21 (vs), hereinafter designated as form J.

In still another preferred embodiment, the present invention comprises a crystalline polymorph J of (6R)-L-erythro-tetrahydrobiopterin dihydrochloride, which exhibits a characteristic X-ray powder diffraction pattern as exhibited in FIG. 10.

The polymorph J is slightly hygroscopic and adsorbs water when handled at air humidity. The polymorph J is a metastable form and a hygroscopic anhydrate, and it can be transformed back into form E from which it is obtained upon exposure to high relative humidity conditions such as above 75% relative humidity. Form J is especially suitable as intermediate and starting material to produce stable polymorph forms. Polymorph form J can be prepared as a solid powder with desired medium particle size range which is typically ranging from 1 μm to about 500 μm.

Still another object of the invention is a crystalline polymorph of (6R)-L-erythro-tetrahydrobiopterin dihydrochloride, which exhibits a characteristic X-ray powder diffraction pattern with characteristic peaks expressed in d-values (Å):

14.0 (s), 6.6 (w), 4.73 (m), 4.64 (m), 3.54 (m), 3.49 (vs), 3.39 (m), 3.33 (vs), 3.13 (s), 3.10 (m), 3.05 (m), 3.01 (m), 2.99 (m), and 2.90 (m), hereinafter designated as form K.

In a more preferred embodiment, the present invention comprises a crystalline polymorph of (6R)-L-erythro-tetrahydrobiopterin dihydrochloride, which exhibits a characteristic X-ray powder diffraction pattern with characteristic peaks expressed in d-values (Å):

14.0 (s), 9.4 (w), 6.6 (w), 6.4 (w), 6.3 (w), 6.1 (w), 6.0 (w), 5.66 (w), 5.33 (w), 5.13 (vw), 4.73 (m), 4.64 (m), 4.48 (w), 4.32 (vw), 4.22 (w), 4.08 (w), 3.88 (w), 3.79 (w), 3.54 (m), 3.49 (vs), 3.39 (m), 3.33 (vs), 3.13 (s), 3.10 (m), 3.05 (m), 3.01 (m), 2.99 (m), and 2.90 (m), hereinafter designated as form K.

In still another preferred embodiment, the present invention comprises a crystalline polymorph K of (6R)-L-erythro-tetrahydrobiopterin dihydrochloride, which exhibits a characteristic X-ray powder diffraction pattern as exhibited in FIG. 11.

The polymorph K is slightly hygroscopic and adsorbs water to a content of about 2.0 percent by weight, which is continuously released between 50° C. and 100° C., when heated at a rate of 10° C./minute. The polymorph K is a meta-stable form and a hygroscopic anhydrate, which is less stable than form B at higher temperatures and form K is especially suitable as intermediate and starting material to produce stable polymorph forms, in particular form B. Polymorph form K can be prepared as a solid powder with desired medium particle size range which is typically ranging from 1 μm to about 500 μm.

2. Hydrate Forms of (6R)-L-erythro-tetrahydrobiopterin dihydrochloride (6R)-L-erythro-tetrahydrobiopterin dihydrochloride forms crystalline hydrate forms C, D, E, H and O, depending from the preparation method.

Still another object of the invention is a crystalline hydrate of (6R)-L-erythro-tetrahydrobiopterin dihydrochloride, which exhibits a characteristic X-ray powder diffraction pattern with characteristic peaks expressed in d-values (Å):

13.9 (vs), 8.8 (m), 6.8 (m), 6.05 (m), 4.25 (m), 4.00 (m), 3.88 (m), 3.80 (m), 3.59 (s), 3.50 (m), 3.44 (m), 3.26 (s), 3.19 (vs), 3.17 (s), 3.11 (m), 2.97 (m), and 2.93 (vs), hereinafter designated as form C.

In a more preferred embodiment, the present invention comprises a crystalline hydrate of (6R)-L-erythro-tetrahydrobiopterin dihydrochloride, which exhibits a characteristic X-ray powder diffraction pattern with characteristic peaks expressed in d-values (Å):

18.2 (m), 15.4 (w), 13.9 (vs), 10.4 (w), 9.6 (w), 9.1 (w), 8.8 (m), 8.2 (w), 8.0 (w), 6.8 (m), 6.5 (w), 6.05 (m), 5.77 (w), 5.64 (w), 5.44 (w), 5.19 (w), 4.89 (w), 4.76 (w), 4.70 (w), 4.41 (w), 4.25 (m), 4.00 (m), 3.88 (m), 3.80 (m), 3.59 (s), 3.50 (m), 3.44 (m), 3.37 (m), 3.26 (s), 3.19 (vs), 3.17 (s), 3.11 (m), 3.06 (m), 3.02 (m), 2.97 (vs), 2.93 (m), 2.89 (m), 2.83 (m), and 2.43 (m), hereinafter designated as form C.

In still another preferred embodiment, the present invention comprises a crystalline hydrate C of (6R)-L-erythro-tetrahydrobiopterin dihydrochloride, which exhibits a characteristic X-ray powder diffraction pattern as exhibited in FIG. 3.

The hydrate form C is slightly hygroscopic and has a water content of approximately 5.5 percent by weight, which indicates that form C is a monohydrate. The hydrate C has a melting point near 94° C. ($\Delta H_f$ is about 31 J/g) and hydrate form C is especially suitable as intermediate and starting material to produce stable polymorphic forms. Polymorph form C can be prepared as a solid powder with desired medium particle size range which is typically ranging from 1 μm to about 500 μm.

Still another object of the invention is a crystalline hydrate of (6R)-L-erythro-tetrahydrobiopterin dihydrochloride, which exhibits a characteristic X-ray powder diffraction pattern with characteristic peaks expressed in d-values (Å):

8.6 (s), 5.56 (m), 4.99 (m), 4.67 (s), 4.32 (m), 3.93 (vs), 3.17 (m), 3.05 (s), 2.88 (m), and 2.79 (m), hereinafter designated as form D.

In a more preferred embodiment, the present invention comprises a crystalline hydrate of (6R)-L-erythro-tetrahydrobiopterin dihydrochloride, which exhibits a characteristic X-ray powder diffraction pattern with characteristic peaks expressed in d-values (Å):

8.6 (s), 6.8 (w), 5.56 (m), 4.99 (m), 4.67 (s), 4.32 (m), 3.93 (vs), 3.88 (w), 3.64 (w), 3.41 (w), 3.25 (w), 3.17 (m), 3.05 (s), 2.94 (w), 2.92 (w), 2.88 (m), 2.85 (w), 2.80 (w), 2.79 (m), 2.68 (w), 2.65 (w), 2.52 (vw), 2.35 (w), 2.34 (w), 2.30 (w), and 2.29 (w), hereinafter designated as form D.

In still another preferred embodiment, the present invention comprises a crystalline hydrate D of (6R)-L-erythro-tetrahydrobiopterin dihydrochloride, which exhibits a characteristic X-ray powder diffraction pattern as exhibited in FIG. 4.

The hydrate form D is slightly hygroscopic and may have a water content of approximately 5.0 to 7.0 percent by weight, which suggests that form D is a monohydrate. The hydrate D has a melting point near 153° C. ($\Delta H_f$ is about 111 J/g) and is of much higher stability than form C and is even stable when exposed to air humidity at ambient temperature. Hydrate form D can therefore either be used to prepare formulations or as intermediate and starting material to produce stable polymorph forms. Polymorph form D can be prepared as a solid powder with desired medium particle size range which is typically ranging from 1 μm to about 500 μm.

Still another object of the invention is a crystalline hydrate of (6R)-L-erythro-tetrahydrobiopterin dihydrochloride, which exhibits a characteristic X-ray powder diffraction pattern with characteristic peaks expressed in d-values (Å):

15.4 (s), 4.87 (w), 3.69 (m), 3.33 (s), 3.26 (vs), 3.08 (m), 2.95 (m), and 2.87 (m), hereinafter designated as form E.

In a more preferred embodiment, the present invention comprises a crystalline hydrate of (6R)-L-erythro-tetrahydrobiopterin dihydrochloride, which exhibits a characteristic X-ray powder diffraction pattern with characteristic peaks expressed in d-values (Å):

15.4 (s), 6.6 (w), 6.5 (w), 5.95 (vw), 5.61 (vw), 5.48 (w), 5.24 (w), 4.87 (w), 4.50 (vw), 4.27 (w), 3.94 (w), 3.78 (w), 3.69 (m), 3.60 (w), 3.33 (s), 3.26 (vs), 3.16 (w), 3.08 (m), 2.98 (w), 2.95 (m), 2.91 (w), 2.87 (m), 2.79 (w), 2.74 (w), 2.69 (w), and 2.62 (w), hereinafter designated as form E.

In still another preferred embodiment, the present invention comprises a crystalline hydrate E of (6R)-L-erythro-tetrahydrobiopterin dihydrochloride, which exhibits a characteristic X-ray powder diffraction pattern as exhibited in FIG. 5.

The hydrate form E has a water content of approximately 10 to 14 percent by weight, which suggests that form E is a dihydrate. The hydrate E is formed at temperatures below room temperature. Hydrate form E is especially suitable as intermediate and starting material to produce stable polymorph forms. It is especially suitable to produce the waterfree form J upon drying under nitrogen or optionally under vacuum. Form E is non-hygroscopic and stable under rather high relative humidities, i.e., at relative humidities above about 60% and up to about 85%. Polymorph form E can be prepared as a solid powder with desired medium particle size range which is typically ranging from 1 μm to about 500 μm.

Still another object of the invention is a crystalline hydrate of (6R)-L-erythro-tetrahydrobiopterin dihydrochloride, which exhibits a characteristic X-ray powder diffraction pattern with characteristic peaks expressed in d-values (Å):

15.8 (vs), 3.87 (m), 3.60 (m), 3.27 (m), 3.21 (m), 2.96 (m), 2.89 (m), and 2.67 (m), hereinafter designated as form H.

In a more preferred embodiment, the present invention comprises a crystalline hydrate of (6R)-L-erythro-tetrahydrobiopterin dihydrochloride, which exhibits a characteristic X-ray powder diffraction pattern with characteristic peaks expressed in d-values (Å):

15.8 (vs), 10.3 (w), 8.0 (w), 6.6 (w), 6.07 (w), 4.81 (w), 4.30 (w), 3.87 (m), 3.60 (m), 3.27 (m), 3.21 (m), 3.13 (w), 3.05 (w), 2.96 (m), 2.89 (m), 2.82 (w), and 2.67 (m), hereinafter designated as form H.

In still another preferred embodiment, the present invention comprises a crystalline hydrate H of (6R)-L-erythrotetrahydrobiopterin dihydrochloride, which exhibits a characteristic X-ray powder diffraction pattern as exhibited in FIG. 8.

The hydrate form H has a water content of approximately 5.0 to 7.0 percent by weight, which suggests that form H is a hygroscopic monohydrate. The hydrate form H is formed at temperatures below room temperature. Hydrate form H is especially suitable as intermediate and starting material to produce stable polymorph forms. Polymorph form H can be prepared as a solid powder with desired medium particle size range which is typically ranging from 1 μm to about 500 μm.

Still another object of the invention is a crystalline hydrate of (6R)-L-erythro-tetrahydrobiopterin dihydrochloride, which exhibits a characteristic X-ray powder diffraction pattern with characteristic peaks expressed in d-values (Å):

8.8 (m), 6.3 (m), 5.65 (m), 5.06 (m), 4.00 (m), 3.88 (m), 3.69 (s), 3.64 (s), 3.52 (vs), 3.49 (s), 3.46 (s), 3.42 (s), 3.32 (m), 3.27 (m), 3.23 (s), 3.18 (s), 3.15 (vs), 3.12 (m), and 3.04 (vs), hereinafter designated as form O.

In a more preferred embodiment, the present invention comprises a crystalline hydrate of (6R)-L-erythro-tetrahydrobiopterin dihydrochloride, which exhibits a characteristic X-ray powder diffraction pattern with characteristic peaks expressed in d-values (Å):

15.9 (w), 14.0 (w), 12.0 (w), 8.8 (m), 7.0 (w), 6.5 (w), 6.3 (m), 6.00 (w), 5.75 (w), 5.65 (m), 5.06 (m), 4.98 (m), 4.92 (m), 4.84 (w), 4.77 (w), 4.42 (w), 4.33 (w), 4.00 (m), 3.88 (m), 3.78 (w), 3.69 (s), 3.64 (s), 3.52 (vs), 3.49 (s), 3.46 (s), 3.42 (s), 3.32 (m), 3.27 (m), 3.23 (s), 3.18 (s), 3.15 (vs), 3.12 (m), 3.04 (vs), 2.95 (m), 2.81 (s), 2.72 (m), 2.67 (m), and 2.61 (m), hereinafter designated as form O.

In still another preferred embodiment, the present invention comprises a crystalline hydrate O of (6R)-L-erythro-tetrahydrobiopterin dihydrochloride, which exhibits a characteristic X-ray powder diffraction pattern as exhibited in FIG. 15.

The hydrate form O is formed at temperatures near room temperature. Hydrate form O is especially suitable as intermediate and starting material to produce stable polymorph forms. Polymorph form O can be prepared as a solid powder with desired medium particle size range which is typically ranging from 1 μm to about 500 μm.

2. Solvate Forms of (6R)-L-erythro-tetrahydrobiopterin dihydrochloride (6R)-L-erythro-tetrahydrobiopterin dihydrochloride forms crystalline solvate forms G, I, L, M and N, depending from the solvent used in the preparation method.

Still another object of the invention is a crystalline ethanol solvate of (6R)-L-erythro-tetrahydrobiopterin dihydrochloride, which exhibits a characteristic X-ray powder diffraction pattern with characteristic peaks expressed in d-values (Å):

14.5 (vs), 7.0 (w), 4.41 (w), 3.63 (m), 3.57 (m), 3.49 (w), 3.41 (m), 3.26 (m), 3.17 (m), 3.07 (m), 2.97 (m), 2.95 (m), 2.87 (w), and 2.61 (w), hereinafter designated as form G.

In a more preferred embodiment, the present invention comprises a crystalline ethanol solvate of (6R)-L-erythro-tetrahydrobiopterin dihydrochloride, which exhibits a characteristic X-ray powder diffraction pattern with characteristic peaks expressed in d-values (Å):

14.5 (vs), 10.9 (w), 9.8 (w), 7.0 (w), 6.3 (w), 5.74 (w), 5.24 (vw), 5.04 (vw), 4.79 (w), 4.41 (w), 4.02 (w), 3.86 (w), 3.77 (w), 3.69 (w), 3.63 (m), 3.57 (m), 3.49 (m), 3.41 (m), 3.26 (m), 3.17 (m), 3.07 (m), 2.97 (m), 2.95 (m), 2.87 (w), and 2.61 (w), hereinafter designated as form G.

In still another preferred embodiment, the present invention comprises a crystalline solvate G of (6R)-L-erythro-tetrahydrobiopterin dihydrochloride, which exhibits a characteristic X-ray powder diffraction pattern as exhibited in FIG. 7.

The ethanol solvate form G has an ethanol content of approximately 8.0 to 12.5 percent by weight, which suggests that form G is a hygroscopic mono ethanol solvate. The solvate form G is formed at temperatures below room temperature. Form G is especially suitable as intermediate and starting material to produce stable polymorph forms. Polymorph form G can be prepared as a solid powder with a desired medium particle size range which is typically ranging from 1 μm to about 500 μm.

Still another object of the invention is a crystalline acetic acid solvate of (6R)-L-erythro-tetrahydrobiopterin dihydrochloride, which exhibits a characteristic X-ray powder diffraction pattern with characteristic peaks expressed in d-values (Å):

14.5 (m), 3.67 (vs), 3.61 (m), 3.44 (m), 3.11 (s), and 3.00 (m), hereinafter designated as form I.

In a more preferred embodiment, the present invention comprises a crystalline acetic acid solvate of (6R)-L-erythro-tetrahydrobiopterin dihydrochloride, which exhibits a characteristic X-ray powder diffraction pattern with characteristic peaks expressed in d-values (Å):

14.5 (m), 14.0 (w), 11.0 (w), 7.0 (vw), 6.9 (vw), 6.2 (vw), 5.30 (w), 4.79 (w), 4.44 (w), 4.29 (w), 4.20 (vw), 4.02 (w), 3.84 (w), 3.80 (w), 3.67 (vs), 3.61 (m), 3.56 (w), 3.44 (m), 3.27 (w), 3.19 (w), 3.11 (s), 3.00 (m), 2.94 (w), 2.87 (w), and 2.80 (w), hereinafter designated as form I.

In still another preferred embodiment, the present invention comprises a crystalline acetic acid solvate I of (6R)-L-erythro-tetrahydrobiopterin dihydrochloride, which exhibits a characteristic X-ray powder diffraction pattern as exhibited in FIG. 9.

The acetic acid solvate form I has an acetic acid content of approximately 12.7 percent by weight, which suggests that form I is a hygroscopic acetic acid mono solvate. The solvate form I is formed at temperatures below room temperature. Acetic acid solvate form I is especially suitable as intermediate and starting material to produce stable polymorph forms. Polymorph form I can be prepared as a solid powder with desired medium particle size range which is typically ranging from 1 μm to about 500 μm.

Still another object of the invention is a crystalline mixed ethanol solvate/hydrate of (6R)-L-erythro-tetrahydrobiopterin dihydrochloride, which exhibits a characteristic X-ray powder diffraction pattern with characteristic peaks expressed in d-values (Å):

14.1 (vs), 10.4 (w), 6.9 (w), 6.5 (w), 6.1 (w), 4.71 (w), 3.46 (m), 3.36 (m), and 2.82 (w), hereinafter designated as form L.

In a more preferred embodiment, the present invention comprises a crystalline mixed ethanol solvate/hydrate of (6R)-L-erythro-tetrahydrobiopterin dihydrochloride, which exhibits a characteristic X-ray powder diffraction pattern with characteristic peaks expressed in d-values (Å):

14.1 (vs), 10.4 (w), 9.5 (w), 9.0 (vw), 6.9 (w), 6.5 (w), 6.1 (w), 5.75 (w), 5.61 (w), 5.08 (w), 4.71 (w), 3.86 (w), 3.78 (w), 3.46 (m), 3.36 (m), 3.06 (w), 2.90 (w), and 2.82 (w), hereinafter designated as form L.

In still another preferred embodiment, the present invention comprises a crystalline mixed ethanol solvate/hydrate L of (6R)-L-erythro-tetrahydrobiopterin dihydrochloride, which exhibits a characteristic X-ray powder diffraction pattern as exhibited in FIG. 12.

Form L may contain 4% but up to 13% ethanol and 0% to about 6% of water. Form L may be transformed into form G when treated in ethanol at temperatures from about 0° C. to 20° C. In addition form L may be transformed into form B when treated in an organic solvent at ambient temperatures (10° C. to 60° C.). Polymorph form L can be prepared as a solid powder with desired medium particle size range which is typically ranging from 1 μm to about 500 μm.

Still another object of the invention is a crystalline ethanol solvate of (6R)-L-erythro-tetrahydrobiopterin dihydrochloride, which exhibits a characteristic X-ray powder diffraction pattern with characteristic peaks expressed in d-values (Å):

18.9 (s), 6.4 (m), and 3.22 (vs), hereinafter designated as form M.

In a more preferred embodiment, the present invention comprises a crystalline ethanol solvate of (6R)-L-erythro-tetrahydrobiopterin dihydrochloride, which exhibits a characteristic X-ray powder diffraction pattern with characteristic peaks expressed in d-values (Å):

18.9 (s), 6.4 (m), 6.06 (w), 5.66 (w), 5.28 (w), 4.50 (w), 4.23 (w), and 3.22 (vs), hereinafter designated as form M.

In still another preferred embodiment, the present invention comprises a crystalline ethanol solvate M of (6R)-L-erythro-tetrahydrobiopterin dihydrochloride, which exhibits a characteristic X-ray powder diffraction pattern as exhibited in FIG. 13.

Form M may contain 4% but up to 13% ethanol and 0% to about 6% of water, which suggests that form M is a slightly hygroscopic ethanol solvate. The solvate form M is formed at room temperature. Form M is especially suitable as intermediate and starting material to produce stable polymorph forms, since form M can be transformed into form G when treated in ethanol at temperatures between about −10° to 15° C., and into form B when treated in organic solvents such as ethanol, C3 and C4 alcohols, or cyclic ethers such as THF and dioxane. Polymorph form M can be prepared as a solid powder with desired medium particle size range which is typically ranging from 1 μm to about 500 μm.

Still another object of the invention is a crystalline polymorph of (6R)-L-erythro-tetrahydrobiopterin dihydrochloride, which exhibits a characteristic X-ray powder diffraction pattern with characteristic peaks expressed in d-values (Å):

19.5 (m), 6.7 (w), 3.56 (m), and 3.33 (vs), 3.15 (w), hereinafter designated as form N.

In a more preferred embodiment, the present invention comprises a crystalline polymorph of (6R)-L-erythro-tetrahydrobiopterin dihydrochloride, which exhibits a characteristic X-ray powder diffraction pattern with characteristic peaks expressed in d-values (Å):

19.5 (m), 9.9 (w), 6.7 (w), 5.15 (w), 4.83 (w), 3.91 (w), 3.56 (m), 3.33 (vs), 3.15 (w), 2.89 (w), 2.81 (w), 2.56 (w), and 2.36 (w), hereinafter designated as form N.

In still another preferred embodiment, the present invention comprises a crystalline polymorph N of (6R)-L-erythro-tetrahydrobiopterin dihydrochloride, which exhibits a characteristic X-ray powder diffraction pattern as exhibited in FIG. 14.

Form N may contain in total up to 10% of isopropanol and water, which suggests that form N is a slightly hygroscopic isopropanol solvate. Form N may be obtained through washing of form D with isopropanol and subsequent drying in vacuum at about 30° C. Form N is especially suitable as intermediate and starting material to produce stable polymorph forms. Polymorph form N can be prepared as a solid powder with desired medium particle size range which is typically ranging from 1 μm to about 500 μm.

For the preparation of the polymorph forms, there may be used crystallisation techniques well known in the art, such as stirring of a suspension (phase equilibration in), precipitation, re-crystallisation, evaporation, solvent like water sorption methods or decomposition of solvates. Diluted, saturated or super-saturated solutions may be used for crystallisation, with or without seeding with suitable nucleating agents. Temperatures up to 100° C. may be applied to form solutions. Cooling to initiate crystallisation and precipitation down to −100° C. and preferably down to −30° C. may be applied. Meta-stable polymorphs or pseudo-polymorphic forms can be used to prepare solutions or suspensions for the preparation of more stable forms and to achieve higher concentrations in the solutions.

4. Preparation of Polymorph Forms of (6R)-L-erythro-tetrahydrobiopterin dihydrochloride

Polymorph Form A

Polymorph form A may be obtained by freeze drying or water removal of solutions of (6R)-L-erythro-tetrahydrobiopterin dihydrochloride in water. A further object of the invention is a process for the preparation of polymorph form A of (6R)-L-erythro-tetrahydrobiopterin dihydrochloride, comprising dissolving (6R)-L-erythro-tetrahydrobiopterin dihydrochloride at ambient temperatures in water, (1) cooling the solution to low temperatures for solidifying the solution, and removing water under reduced pressure, or (2) removing water from said aqueous solution.

The crystalline form A can be isolated by filtration and then dried to evaporate absorbed water from the product. Drying conditions and methods are known and drying of the isolated product or water removal pursuant to variant (2) according to the invention may be carried out in applying elevated temperatures, for example up to 80° C., preferably in the range from 30° C. to 80° C., under vacuum or elevated temperatures and vacuum. Prior to isolation of a precipitate obtained in variant (2), the suspension may be stirred for a certain time for phase equilibration. The concentration of (6R)-L-erythro-tetrahydrobiopterin dihydrochloride in the aqueous solution may be from 5 to 40 percent by weight, referred to the solution.

Ambient temperatures may mean a range from 30 to 120° C. Low temperatures may mean temperatures below −40° C. and preferably below −60° C. and to −180° C. A fast cooling is preferred to obtain solid solutions as starting material. A reduced pressure is applied until the solvent is completely removed. Freeze drying is a technology well known in the art. The time to complete solvent removal is dependent on the applied vacuum, which may be from 0.01 to 1 mbar, the solvent used and the freezing temperature.

Polymorph form A is stable at room temperature or below room temperature under substantially water free conditions, which is demonstrated with phase equilibration tests of suspensions in tetrahydrofuran or tertiary-butyl methyl ether stirred for five days and 18 hours respectively under nitrogen at room temperature. Filtration and air drying at room temperature yields unchanged polymorph form A.

Polymorph B

All crystal forms (polymorphs, hydrates and solvates), inclusive crystal form B, can be used for the preparation of the most stable polymorph B.

Polymorph B may be obtained by phase equilibration of suspensions of amorphous or other forms than polymorph form B, such as polymorph A, in suitable polar and non aqueous solvents. The present invention also refers to a process for the preparation of polymorph form B of (6R)-L-erythro-tetrahydrobiopterin dihydrochloride, comprising dispersion of particles of a solid form, preferably other than form B, of (6R)-L-erythro-tetrahydrobiopterin dihydrochloride in a solvent at room temperature, stirring the suspension at ambient temperatures for a time sufficient to produce polymorph form B, thereafter isolating crystalline form B and removing the solvent from the isolated form B.

Ambient temperatures may mean temperatures in a range from 0° C. to 60° C., preferably 20° C. to 40° C. The applied temperature may be changed during treatment and stirring by decreasing the temperature stepwise or continuously. Suitable solvents are for example methanol, ethanol, isopropanol, other $C_3$- and $C_4$-alcohols, acetic acid, acetonitrile, tetrahydrofurane, methyl-t-butyl ether, 1,4-dioxane, ethyl acetate, isopropyl acetate, other $C_3$-$C_6$-acetates, methyl ethyl ketone and other methyl-$C_3$-$C_5$alkyl-ketones. The time to complete phase equilibration may be up to 30 hours and preferably up to 20 hours or less than 20 hours.

Polymorph B may also be obtained by crystallisation from solvent mixtures containing up to about 5% water, especially from mixtures of ethanol, acetic acid and water. The present invention also refers to a process for the preparation of polymorph form B of (6R)-L-erythro-tetrahydrobiopterin dihydrochloride, comprising dissolution, optionally at elevated temperatures, preferably of a solid lower energy form than form B or of form B of (6R)-L-erythro-tetrahydrobiopterin dihydrochloride in a solvent mixture comprising ethanol, acetic acid and water, addition of seeds to the solution, cooling the obtained suspension and isolation of the formed crystals.

Dissolution may be carried out at room temperature or up to 70° C., preferably up to 50° C. There may be used the final solvent mixture for dissolution or the starting material may be first dissolved in water and the other solvents may than be added both or one after the other solvent. The composition of the solvent mixture may comprise a volume ratio of water: acetic acid:tetrahydrofurane of 1:3:2 to 1:9:4 and preferably 1:5:4. The solution is preferably stirred. Cooling may mean temperatures down to −40° C. to 0° C., preferably down to 10° C. to 30° C. Suitable seeds are polymorph form B from another batch or crystals having a similar or identical morphology. After isolation, the crystalline form B can be washed with a non-solvent such as acetone or tetrahydrofurane and dried in usual manner.

Polymorph B may also be obtained by crystallisation from aqueous solutions through the addition of non-solvents such as methanol, ethanol and acetic acid. The crystallisation and isolation procedure can be advantageously carried out at room temperature without cooling the solution. This process is therefore very suitable to be carried out at an industrial scale.

In a preferred embodiment, the present invention refers to a process for the preparation of polymorph form B of (6R)-L-erythro-tetrahydrobiopterin dihydrochloride, comprising dissolution of a solid form other than form B or of form B of (6R)-L-erythro-tetrahydrobiopterin dihydrochloride in water at ambient temperatures, adding a non-solvent in an amount sufficient to form a suspension, optionally stirring the suspension for a certain time, and thereafter isolation of the formed crystals.

A crystallization experiment from solution can be followed by a subsequent suspension equilibration under ambient conditions.

Ambient temperatures may mean a temperature in the range of 10 to 40° C., and most preferably room temperature. The concentration of (6R)-L-erythro-tetrahydrobiopterin dihydrochloride in the aqueous solution may be from 10 to 80 percent by weight, more preferably from 20 to 60 percent by weight, referred to the solution. Preferred non-solvents are methanol, ethanol and acetic acid. The non-solvent may be added to the aqueous solution. More preferably, the aqueous solution is added to the non-solvent. The stirring time after formation of the suspension may be up to 30 hours and preferably up to 20 hours or less than 20 hours. Isolation by filtration and drying is carried out in known manner as described before.

Polymorph form B is a very stable crystalline form, that can be easily filtered off, dried and ground to particle sizes desired for pharmaceutical formulations. These outstanding properties renders polymorph form B especially feasible for pharmaceutical application.

Polymorph F

Polymorph F may be obtained by phase equilibration of suspensions of polymorph form A in suitable polar and non-aqueous solvents, which scarcely dissolve said lower energy forms, especially alcohols such as methanol, ethanol, propanol and isopropanol. The present invention also refers to a process for the preparation of polymorph form F of (6R)-L-erythro-tetrahydrobiopterin dihydrochloride, comprising dispersion of particles of solid form A of (6R)-L-erythro-tetrahydrobiopterin dihydrochloride in a non-aqueous solvent that scarcely dissolves said (6R)-L-erythro-tetrahydrobiopterin dihydrochloride below room temperature, stirring the suspension at said temperatures for a time sufficient to produce polymorph form F, thereafter isolating crystalline form F and removing the solvent from the isolated form F. Removing of solvent and drying may be carried out under air, dry air or a dry protection gas such as nitrogen or noble gases and at or below room temperature, for example down to 0° C. The temperature during phase equilibration is preferably from 5 to 15° C. and most preferably about 10° C.

Polymorph J

Polymorph J may be obtained by dehydration of form E at moderate temperatures under vacuum. The present invention also refers to a process for the preparation of polymorph form J of (6R)-L-erythro-tetrahydrobiopterin dihydrochloride, comprising preparation of form E and removing the water from form E by treating form E in a vacuum drier to obtain form J at moderate temperatures which may mean a temperature in the range of 25 to 70° C., and most preferably 30 to 50° C.

Polymorph K

Polymorph K may be obtained by crystallization from mixtures of polar solvents containing small amounts of water and in the presence of small amounts of ascorbic acid. Solvents for the solvent mixture may be selected from acetic acid and an alcohol such as methanol, ethanol, n- or isopropanol. The present invention also refers to a process for the preparation of polymorph form K of (6R)-L-erythro-tetrahydrobiopterin dihydrochloride, comprising dissolving (6R)-L-erythro-tetrahydrobiopterin dihydrochloride in a mixture of acetic acid and an alcohol or tetrahydrofurane containing small amounts of water and a small amount of ascorbic acid at elevated temperatures, lowering temperature below room temperature to crystallise said dihydrochloride, isolating the precipitate and drying the isolated precipitate at elevated temperature optionally under vacuum. Suitable alcohols are for example methanol, ethanol, propanol and isopropanol, whereby ethanol is preferred. The ratio of acetic acid to alcohol or tetrahydrofurane may be from 2:1 to 1:2 and preferably about 1:1. Dissolution of (6R)-L-erythro-tetrahydrobiopterin dihydrochloride can be carried out in presence of a higher water content and more of the antisolvent mixture can be added to obtain complete precipitation. The amount of water in the final composition may be from 0.5 to 5 percent by weight and the amount of ascorbic acid may be from 0.01 to 0.5 percent by weight, both referred to the solvent mixture. The temperature for dissolution may be in the range from 30 to 100 and preferably 35 to 70° C. and the drying temperature may be in the range from 30 to 50° C. The precipitate may be washed with an alcohol such as ethanol after isolation, e.g. filtration. The polymorph K can easily be converted in the most stable form B by phase equilibration in e.g. isopropanol and optionally seeding with form B crystals at above room temperature such as temperatures from 30 to 40° C.

5. Preparation of Hydrate Forms of (6R)-L-erythro-tetrahydrobiopterin dihydrochloride

Form C

Hydrate form C may be obtained by phase equilibration at ambient temperatures of a polymorph form such as polymorph B suspension in a non-solvent which contains water in an amount of preferably about 5 percent by weight, referred to the solvent. The present invention also refers to a process for the preparation of hydrate form C of (6R)-L-erythro-tetrahydrobiopterin dihydrochloride, comprising suspending (6R)-L-erythro-tetrahydrobiopterin dihydrochloride in a non-solvent such as heptane, $C_1$-$C_4$-alcohols such as methanol, ethanol, 1- or 2-propanol, acetates, such as ethyl acetate, acetonitrile, acetic acid or ethers such as tetrahydrofuran, dioxane, tertiary-butyl methyl ether, or binary or ternary mixtures of such non-solvents, to which sufficient water is added to form a monohydrate, and stirring the suspension at or below ambient temperatures (e.g. 0 to 30° C.) for a time sufficient to form a monohydrate. Sufficient water may mean from 1 to 10 and preferably from 3 to 8 percent by weight of water, referred to the amount of solvent. The solids may be filtered off and dried in air at about room temperature. The solid can absorb some water and therefore possess a higher water content than the theoretical value of 5.5 percent by weight. Hydrate form C is unstable with respect to forms D and B, and easily converted to polymorph form B at temperatures of about 40° C. in air and lower relative humidity. Form C can be transformed into the more stable hydrate D by suspension equilibration at room temperature.

Form D

Hydrate form D may be obtained by adding at about room temperature concentrated aqueous solutions of (6R)-L-erythro-tetrahydrobiopterin dihydrochloride to an excess of a non-solvent such as hexane, heptane, dichloromethane, 1- or 2-propanol, acetone, ethyl acetate, acetonitril, acetic acid or ethers such as tetrahydrofuran, dioxane, tertiary-butyl methyl ether, or mixtures of such non-solvents, and stirring the suspension at ambient temperatures. The crystalline solid can be filtered off and then dried under dry nitrogen at ambient temperatures. A preferred non-solvent is isopropanol. The addition of the aqueous solution may carried out drop-wise to avoid a sudden precipitation. The present invention also refers to a process for the preparation of hydrate form D of (6R)-L-erythro-tetrahydrobiopterin dihydrochloride, comprising adding at about room temperature a concentrated aqueous solutions of (6R)-L-erythro-tetrahydrobiopterin dihydrochloride to an excess of a non-solvent and stirring the suspension at ambient temperatures. Excess of non-solvent may mean a ratio of aqueous to the non solvent from 1:10 to 1:1000. Form D contains a small excess of water, related to the monohydrate, and it is believed that it is absorbed water due to the slightly hygroscopic nature of this crystalline hydrate. Hydrate form D is deemed to be the most stable one under the known hydrates at ambient temperatures and a relative humidity of less than 70%. Hydrate form D may be used for formulations prepared under conditions, where this hydrate is stable. Ambient temperature may mean 20 to 30° C.

Hydrate Form E

Hydrate form E may be obtained by adding concentrated aqueous solutions of (6R)-L-erythro-tetrahydrobiopterin dihydrochloride to an excess of a non-solvent cooled to temperatures from about 10 to −10° C. and preferably between 0 to 10° C. and stirring the suspension at said temperatures. The crystalline solid can be filtered off and then dried under dry nitrogen at ambient temperatures. Non-solvents are for example such as hexane, heptane, dichloromethane, 1- or 2-propanol, acetone, ethyl acetate, acetonitrile, acetic acid or ethers such as tetrahydrofuran, dioxane, tertiary-butyl methyl ether, or mixtures of such non-solvents. A preferred non-solvent is isopropanol. The addition of the aqueous solution may carried out drop-wise to avoid a sudden precipitation. The present invention also refers to a process for the preparation of hydrate form E of (6R)-L-erythro-tetrahydrobiopterin dihydrochloride, comprising adding a concentrated aqueous solutions of (6R)-L-erythro-tetrahydrobiopterin dihydrochloride to an excess of a non-solvent which is cooled to temperatures from about 10 to −10° C., and stirring the suspension at ambient temperatures. Excess of non-solvent may mean a ratio of aqueous to the non solvent from 1:10 to 1:1000. A preferred non-solvent is tetrahydrofuran. Another preparation process comprises exposing polymorph form B to an air atmosphere with a relative humidity of 70 to 90%, preferably about 80%. Hydrate form E is deemed to be a dihydrate, whereby some additional water may be absorbed. Polymorph form E can be transformed into polymorph J upon drying under vacuum at moderate temperatures, which may mean between 20° C. and 50° C. at pressures between 0 and 100 mbar. Form E is especially suitable for formulations in semi solid forms because of its stability at high relative humidities.

Form H

Hydrate form H may be obtained by dissolving at ambient temperatures (6R)-L-erythro-tetrahydrobiopterin dihydrochloride in a mixture of acetic acid and water, adding then a non-solvent to precipitate a crystalline solid, cooling the obtained suspension and stirring the cooled suspension for a certain time. The crystalline solid is filtered off and then dried under vacuum at ambient temperatures. Non-solvents are for example such as hexane, heptane, dichloromethane, 1- or 2-propanol, acetone, ethyl acetate, acetonitrile, acetic acid or ethers such as tetrahydrofuran, dioxane, tertiary-butyl methyl ether, or mixtures of such non-solvents. A preferred non-solvent is tetrahydrofuran. The present invention also refers to a process for the preparation of hydrate form H of (6R)-L-erythro-tetrahydrobiopterin dihydrochloride, comprising dissolving at ambient temperatures (6R)-L-erythro-tetrahydrobiopterin dihydrochloride in a mixture of acetic acid and a less amount than that of acetic acid of water, adding a non-solvent and cooling the obtained suspension to temperatures in the range of 10 to 10° C., and preferably −5 to 5° C., and stirring the suspension at said temperature for a certain time. Certain time may mean 1 to 20 hours. The weight ratio of acetic acid to water may be from 2:1 to 25:1 and preferably 5:1 to 15:1. The weight ratio of acetic acid/water to the non-solvent may be from 1:2 to 1:5. Hydrate form H seems to be a monohydrate with a slight excess of water absorbed due to the hygroscopic nature.

Form O

Hydrate form O can be prepared by exposure of polymorphic form F to a nitrogen atmosphere containing water vapour with a resulting relative humidity of about 52% for about 24 hours. The fact that form F, which is a slightly hygroscopic anhydrate, can be used to prepare form O under 52% relative humidity suggests that form O is a hydrate, which is more stable than form F under ambient temperature and humidity conditions.

6. Preparation of Solvate Forms of (6R)-L-erythro-tetrahydrobiopterin dihydrochloride Form G Ethanol solvate form G may be obtained by crystallisation of L-erythro-tetrahydrobiopterin dihydrochloride dissolved in water and adding a large excess of ethanol, stirring the obtained suspension at or below ambient temperatures and drying the isolated solid under air or nitrogen at about room temperature. Here, a large excess of ethanol means a resulting mixture of ethanol and water with less than 10% water, preferably about 3 to 6%. The present invention also refers to a process for the preparation of ethanolate form G of (6R)-L-erythro-tetrahydrobiopterin dihydrochloride, comprising dissolving at about room temperature to temperatures of 75° C. (6R)-L-erythro-tetrahydrobiopterin dihydrochloride in water or in a mixture of water and ethanol, cooling a heated solution to room temperature and down to 5 to 10° C., adding optionally ethanol to complete precipitation, stirring the obtained suspension at temperatures of 20 to 5° C., filtering off the white, crystalline solid and drying the solid under air or a protection gas such as nitrogen at temperatures about room temperature. The process may be carried out in a first variant in dissolving (6R)-L-erythro-tetrahydrobiopterin dihydrochloride at about room temperature in a lower amount of water and then adding an excess of ethanol and then stirring the obtained suspension for a time sufficient for phase equilibration. In a second variant, (6R)-L-erythro-tetrahydrobiopterin dihydrochloride may be suspended in ethanol, optionally adding a lower amount of water, and heating the suspension and dissolute (6R)-L-erythro-tetrahydrobiopterin dihydrochloride, cooling down the solution to temperatures of about 5 to 15° C., adding additional ethanol to the suspension and then stirring the obtained suspension for a time sufficient for phase equilibration.

Form I

Acetic acid solvate form I may be obtained by dissolution of L-erythro-tetrahydrobiopterin dihydrochloride in a mixture of acetic acid and water at elevated temperature, adding further acetic acid to the solution, cooling down to a temperature of about 10° C., then warming up the formed suspension to about 15° C., and then stirring the obtained suspension for a time sufficient for phase equilibration, which may last up to 3 days. The crystalline solid is then filtered off and dried under air or a protection gas such as nitrogen at temperatures about room temperature.

Form L

Form L may be obtained by suspending hydrate form E at room temperature in ethanol and stirring the suspension at temperatures from 0 to 10° C., preferably about 5° C., for a time sufficient for phase equilibration, which may be 10 to 20 hours. The crystalline solid is then filtered off and dried preferably under reduced pressure at 30° C. or under nitrogen. Analysis by TG-FTIR suggests that form L may contain variable amounts of ethanol and water, i.e. it can exist as an polymorph (anhydrate), as a mixed ethanol solvate/hydrate, or even as a hydrate.

Form M

Ethanol solvate form M may be obtained by dissolution of L-erythro-tetrahydrobiopterin dihydrochloride in ethanol and evaporation of the solution under nitrogen at ambient temperature, i.e., between 10° C. and 40° C. Form M may also be obtained by drying of form G under a slight flow of dry nitrogen at a rate of about 20 to 100 ml/min. Depending on the extent of drying under nitrogen, the remaining amount of ethanol may be variable, i.e. from about 3% to 13%.

Form N

The isopropanol form N may be obtained by dissolution of L-erythro-tetrahydrobiopterin dihydrochloride in 4.0 ml of a mixture of isopropanol and water (mixing volume ratio for example 4:1). To this solution is slowly added isopropanol (IPA, for example about 4.0 ml) and the resulting suspension is cooled to 0° C. and stirred for several hours (e.g. about 10 to 18 hours) at this temperature. The suspension is filtered and the solid residue washed with isopropanol at room temperature. The obtained crystalline material is then dried at ambient temperature (e.g. about 20 to 30° C.) and reduced pressure (about 2 to 10 mbar) for several hours (e.g. about 5 to 20 hours). TG-FTIR shows a weight loss of 9.0% between 25 to 200° C., which is attributed to both isopropanol and water. This result suggests that form N can exist either in form of an isopropanol solvate, or in form of mixed isopropanol solvate/hydrate, or as an non-solvated form containing a small amount of water.

A further object of the invention is a pharmaceutical composition comprising solid crystal forms of (6R)-L-erythro-tetrahydrobiopterin dihydrochloride selected from the group consisting of forms A, B, D, E, F, J, K, L and 0 or a combination thereof, and a pharmaceutically acceptable carrier or diluent.

As mentioned above, it was found that crystal form B is the most stable form of all found crystal forms. Crystal form B is especially suitable for various types and a broad range of formulations, even in presence of humid components without formation of hydrates.

Accordingly, this invention is also directed to a pharmaceutical composition comprising a pure polymorph form B of (6R)-L-erythro-tetrahydrobiopterin dihydrochloride and a pharmaceutically acceptable carrier or diluent.

In principle, also forms A, D, E, F, J, K, L and O are suitable for use in pharmaceutical formulations and accordingly, this invention is also directed to a pharmaceutical composition comprising forms A, D, E, F, J, K, L and O of (6R)-L-erythro-tetrahydrobiopterin dihydrochloride and a pharmaceutically acceptable carrier or diluent. For forms A, F, J, K and L are preferably used dry formulation components and products may be kept in sealed containers, mainly to avoid formation of hydrates. Hydrate forms D, E and O can be used directly in presence of humid components for the formulation and air humidity must not be excluded.

It was surprisingly found that hydrate form D is the most stable form under the hydrates and forms B and D are especially suitable to be used in pharmaceutical formulations. Forms B and D presents some advantages like an aimed manufacture, good handling due to convenient crystal size and morphology, very good stability under production conditions of various types of formulation, storage stability, higher solubility, and high bio-availability.

Accordingly, this invention is particularly directed to a pharmaceutical composition comprising polymorph form B or hydrate form D of (6R)-L-erythro-tetrahydrobiopterin dihydrochloride and a pharmaceutically acceptable carrier or diluent.

In the following, crystal form is meaning A, B, D, E, F, J, K, L and O.

The amount of crystal forms of (6R)-L-erythro-tetrahydrobiopterin dihydrochloride substantially depends on type of formulation and desired dosages during administration time periods. The amount in an oral formulation may be from 0.1 to 50 mg, preferably from 0.5 to 30 mg, and more preferably from 1 to 15 mg.

The crystal forms of (6R)-L-erythro-tetrahydrobiopterin dihydrochloride may be used together with folates such as, folic acid, or tetrahydrofolates. Examples of tetrahydrofolates are tetrahydrofolic acid, 5,10-methylenetetrahydrofolic acid, 10-formyltetrahydrofolic acid, 5-formyltetrahydrofolic acid or preferably 5-methyltetrahydrofolic acid, their polyglutamates, their optically pure diastereoisomers, but also mixtures of diastereoisomers, especially the racemic mixture, pharmaceutically acceptable salts such as sodium, potassium, calcium or ammonium salts, each alone, in combination with an other folate or additionally with arginine. The weight ratio of crystal forms:folic acids or salts thereof: arginine may be from 1:10:10 to 10:1:1.

Oral formulations may be solid formulations such as capsules, tablets, pills and troches, or liquid formulations such as aqueous suspensions, elixirs and syrups. Solid and liquid formulations encompass also incorporation of crystal forms of (6R)-L-erythro-tetrahydrobiopterin dihydrochloride according to the invention into liquid or solid food. Liquids also encompass solutions of (6R)-L-erythro-tetrahydrobiopterin dihydrochloride for parenteral applications such as infusion or injection.

The crystal form according to the invention may be directly used as powder (micronized particles), granules, suspensions or solutions, or it may be combined together with other pharmaceutically acceptable ingredients in admixing the components and optionally finely divide them, and then filling capsules, composed for example from hard or soft gelatine, compressing tablets, pills or troches, or suspend or dissolve them in carriers for suspensions, elixirs and syrups. Coatings may be applied after compression to form pills.

Pharmaceutically acceptable ingredients are well known for the various types of formulation and may be for example binders such as natural or synthetic polymers, excipients, lubricants, surfactants, sweetening and flavouring agents, coating materials, preservatives, dyes, thickeners, adjuvants, antimicrobial agents, antioxidants and carriers for the various formulation types.

Examples for binders are gum tragacanth, acacia, starch, gelatine, and biological degradable polymers such as homo- or co-polyesters of dicarboxylic acids, alkylene glycols, polyalkylene glycols and/or aliphatic hydroxylcarboxylic acids; homo- or co-polyamides of dicarboxylic acids, alkylene diamines, and/or aliphatic amino carboxylic acids; corresponding polyester-polyamide-co-polymers, polyanhydrides, polyorthoesters, polyphosphazene and polycarbonates. The biological degradable polymers may be linear, branched or crosslinked. Specific examples are poly-glycolic acid, poly-lactic acid, and poly-d,l-lactide/glycolide. Other examples for polymers are water-soluble polymers such as polyoxaalkylenes (polyoxaethylene, polyoxapropylene and mixed polymers thereof, poly-acrylamides and hydroxylalkylated polyacrylamides, poly-maleic acid and esters or -amides thereof, poly-acrylic acid and esters or -amides thereof, poly-vinylalcohol und esters or -ethers thereof, polyvinylimidazole, polyvinylpyrrolidon, und natural polymers like chitosan.

Examples for excipients are phosphates such as dicalcium phosphate.

Examples for lubricants are natural or synthetic oils, fats, waxes, or fatty acid salts like magnesium stearate.

Surfactants may be anionic, anionic, amphoteric or neutral. Examples for surfactants are lecithin, phospholipids, octyl sulfate, decyl sulfate, dodecyl sulfate, tetradecyl sulfate, hexadecyl sulfate and octadecyl sulfate, Na oleate or Na caprate, 1-acylaminoethane-2-sulfonic acids, such as 1-octanoylaminoethane-2-sulfonic acid, 1-decanoylaminoethane-2-sulfonic acid, 1-dodecanoylaminoethane-2-sulfonic acid, 1-tetradecanoylaminoethane-2-sulfonic acid, 1-hexadecanoylaminoethane-2-sulfonic acid, and 1-octadecanoylaminoethane-2-sulfonic acid, and taurocholic acid and taurodeoxycholic acid, bile acids and their salts, such as cholic acid, deoxycholic acid and sodium glycocholates, sodium caprate or sodium laurate, sodium oleate, sodium lauryl sulphate, sodium cetyl sulphate, sulfated castor oil and sodium dioctylsulfosuccinate, cocamidopropylbetaine and laurylbetaine, fatty alcohols, cholesterols, glycerol mono- or -distearate, glycerol mono- or -dioleate and glycerol mono- or -dipalmitate, and polyoxyethylene stearate.

Examples for sweetening agents are sucrose, fructose, lactose or aspartame.

Examples for flavouring agents are peppermint, oil of wintergreen or fruit flavours like cherry or orange flavour.

Examples for coating materials are gelatine, wax, shellac, sugar or biological degradable polymers.

Examples for preservatives are methyl or propylparabens, sorbic acid, chlorobutanol, phenol and thimerosal.

Examples for adjuvants are fragrances.

Examples for thickeners are synthetic polymers, fatty acids and fatty acid salts and esters and fatty alcohols.

Examples for antioxidants are vitamins, such as vitamin A, vitamin C, vitamin D or vitamin E, vegetable extracts or fish oils.

Examples for liquid carriers are water, alcohols such as ethanol, glycerol, propylene glycol, liquid polyethylene glycols, triacetin and oils. Examples for solid carriers are talc, clay, microcrystalline cellulose, silica, alumina and the like.

The formulation according to the invention may also contain isotonic agents, such as sugars, buffers or sodium chloride.

The hydrate form D according to the invention may also be formulated as effervescent tablet or powder, which disintegrate in an aqueous environment to provide a drinking solution.

A syrup or elixir may contain the polymorph of the invention, sucrose or fructose as sweetening agent a preservative like methylparaben, a dye and a flavouring agent.

Slow release formulations may also be prepared from the polymorph according to the invention in order to achieve a controlled release of the active agent in contact with the body fluids in the gastro intestinal tract, and to provide a substantial constant and effective level of the active agent in the blood plasma. The crystal form may be embedded for this purpose in a polymer matrix of a biological degradable polymer, a water-soluble polymer or a mixture of both, and optionally suitable surfactants. Embedding can mean in this context the incorporation of micro-particles in a matrix of polymers. Controlled release formulations are also obtained through encapsulation of dispersed micro-particles or emulsified micro-droplets via known dispersion or emulsion coating technologies.

The crystal form of this invention is also useful for administering a combination of therapeutic effective agents to an animal. Such a combination therapy can be carried out in using at least one further therapeutic agent which can be additionally dispersed or dissolved in a formulation.

The crystal form of this invention and its formulations respectively can be also administered in combination with other therapeutic agents that are effective to treat a given condition to provide a combination therapy.

The crystal form and the pharmaceutical composition according to the invention are highly suitable for effective treatment of neurological disorders.

Another object of the invention is a method of delivering crystal forms of (6R)-L-erythro-tetrahydrobiopterin dihydrochloride according to the invention to a host, comprising administering to a host an effective amount of a polymorph according to the invention.

A further object of the invention is the use of crystal forms of (6R)-L-erythro-tetrahydrobiopterin dihydrochloride for the manufacture of a medicament useful in the treatment of neurological disorders.

The following examples illustrate the invention without limiting the scope.

A) Preparation of Polymorph Forms

Within the Examples A1, A5, A6 and A7 (6R)-L-erythro-tetrahydrobiopterin dihydrochloride from Schircks Laboratories, CH-8645 Jona, Switzerland was used as starting material.

EXAMPLE A1

Preparation of Polymorph Form A of (6R)-L-erythro-tetrahydrobiopterin dihydrochloride 1.05 gram of (6R)-L-erythro-tetrahydrobiopterin dihydrochloride are dissolved in 4.0 ml of bi-distilled water at 23±2° C. The solution is filtrated through a 0.22 μm millipore filtration unit and the filtrate is transferred into a 250 ml round flask. The solution in this flask is frozen by placing the flask into a bed with solid carbon dioxide at −78° C. The flask with the frozen content is then connected to a laboratory freeze dryer operating at a starting pressure of about 0.05 mbar. After about 20 hours the freeze drying is complete and the vacuum flask is disconnected from the freeze dryer and about 1.0 g of white, crystalline solid material is obtained. Investigation of the obtained solid by powder X-ray diffraction reveals form A, which shows the powder X-ray diffraction pattern as exhibited in table 1 and FIG. 1. Further investigation of the obtained solid by thermogravimetry coupled with infrared spectroscopy at a heating rate of 10° C./minute reveals a water content of about 3% with a nearly continuous release of the water between 50° C. and 200° C. The sample begins to decompose above 200° C.

TABLE 1

D-Spacing for form A

| Angle [°2θ] | d-spacings [Å] | Intensity (qualitative) |
|---|---|---|
| 5.7 | 15.5 | vs |
| 7.4 | 12.0 | m |
| 13.3 | 6.7 | m |
| 13.6 | 6.5 | m |
| 14.0 | 6.3 | w |
| 14.4 | 6.1 | w |
| 14.9 | 5.96 | w |
| 16.1 | 5.49 | m |
| 18.1 | 4.89 | m |
| 23.5 | 3.79 | m |
| 24.0 | 3.70 | s |
| 25.6 | 3.48 | m |
| 25.8 | 3.45 | m |
| 26.8 | 3.33 | s |
| 27.3 | 3.26 | s |
| 27.7 | 3.22 | m |
| 28.1 | 3.18 | m |
| 28.9 | 3.08 | m |
| 29.6 | 3.02 | w |
| 30.3 | 2.95 | w |
| 31.1 | 2.87 | m |
| 32.1 | 2.79 | w |
| 33.2 | 2.70 | w |

EXAMPLE A2

Stability of Polymorph Form A 105 mg of polymorph A according to example A1 are suspended in 1.0 ml tertiary butyl methyl ether (TBME). The suspension is stirred under nitrogen atmosphere for about 18 hours at room temperature, filtrated and the white solid residue is then dried under air. Yield: 103 mg of crystalline white solid, which essentially still corresponds to form A according to FT Raman spectrum and X-ray diffraction pattern.

EXAMPLE A3

Stability of Polymorph Form A 90 mg of polymorph A according to example A1 are suspended in 2.0 ml tetrahydrofuran (THF) and the resulting suspension is stirred in air for five days at room temperature, filtrated and the white solid residue is then dried under air. Yield: 85 mg of crystalline white solid, which still corresponds to form A according to FT Raman spectrum and X-ray diffraction pattern.

EXAMPLE A4

Preparation of Polymorph Form B of (6R)-L-erythro-tetrahydrobiopterin dihydrochloride from Polymorph Form A 94 mg of (6R)-L-erythro-tetrahydrobiopterin dihydrochloride as polymorph form A according to example A1 are suspended in 1.0 ml of ethanol in a 4.0 ml glass vial under nitrogen. The obtained suspension is stirred at a temperature of 23° C. for about 18 hours. After that time the white suspension is filtrated and the obtained crystalline solid is dried at 23° C. under nitrogen atmosphere for about 1 hour. Investigation of the obtained solid by powder X-ray diffraction reveals a crystalline form B, which shows the powder X-ray diffraction pattern as exhibited in table 2 and in FIG. 2.

TABLE 2

D-Spacing for form B

| Angle [°2θ] | d-spacings [Å] | Intensity (qualitative) |
|---|---|---|
| 10.1 | 8.7 | vs |
| 12.9 | 6.9 | w |
| 15.0 | 5.90 | vw |
| 15.7 | 5.63 | m |
| 17.5 | 5.07 | m |
| 18.6 | 4.76 | m |
| 20.1 | 4.40 | m |
| 21.4 | 4.15 | w |
| 22.2 | 4.00 | s |
| 22.5 | 3.95 | m |
| 25.3 | 3.52 | m |
| 25.8 | 3.44 | w |
| 26.8 | 3.32 | m |
| 27.6 | 3.23 | s |
| 28.1 | 3.17 | w |
| 28.7 | 3.11 | vs |
| 29.2 | 3.06 | w |
| 29.9 | 2.99 | w |
| 30.1 | 2.96 | w |
| 30.4 | 2.94 | m |
| 31.2 | 2.87 | w |
| 31.5 | 2.84 | s |
| 31.7 | 2.82 | m |
| 33.3 | 2.69 | w |
| 34.7 | 2.59 | w |
| 36.9 | 2.44 | w |

EXAMPLE A5

Preparation of Polymorph Form B of (6R)-L-erythro-tetrahydrobiopterin dihydrochloride 337 mg of (6R)-L-erythro-tetrahydrobiopterin dihydrochloride are dissolved in 0.5 ml of bi-distilled water. 300 μl of this aqueous solution are added drop wise into a 22 ml glass vial containing 10.0 ml of ethanol. Upon addition of the aqueous solution to the ethanol, a white suspension is formed that is further stirred at 23° C. for about 15 hours. Thereafter a white, crystalline material is obtained by filtration and drying under nitrogen at 23° C. for about 1 hour. Yield is 74 mg. Investigation of the obtained solid reveals a powder X-ray diffraction pattern and Raman spectrum, which are identical to those described in example A4.

EXAMPLE A6

Preparation of Polymorph Form B of (6R)-L-erythro-tetrahydrobiopterin dihydrochloride 337 mg of (6R)-L-erythro-tetrahydrobiopterin dihydrochloride are dissolved in 0.5 ml of bi distilled water. 300 μl of this aqueous solution are added drop-wise into a 22 ml glass vial containing 10.0 ml of acetic acid. Upon addition of the aqueous solution to the acetic acid, a white suspension is formed that is further stirred at 23° C. for about 15 hours. Thereafter a white crystalline material is obtained by filtration and drying under nitrogen for about 2 hours and 23° C. Yield is 118 mg. Investigation of the obtained solid by Raman spectroscopy reveals an identical spectrum as described in example A4.

EXAMPLE A7

Preparation of Polymorph Form B of (6R)-L-erythro-tetrahydrobiopterin dihydrochloride 1.0 g of (6R)-L-erythro-tetrahydrobiopterin dihydrochloride are added to 4 ml bi-distilled water in a test-tube. This aqueous solution is added to 20 ml 100% acetic acid in a glass vial at room temperature. A gelatine-like precipitate is formed that dissolves within several minutes. Then 16 ml tetrahydrofurane are added and the solution is seeded with polymorph B crystals. A suspension is formed during stirring for 10 minutes at room temperature. This suspension is cooled to 0° C. and stands then for 1 hour at this temperature. The precipitate is filtered off, washed with tetrahydrofurane and then dried under vacuum for 17 hours at 20° C. and 10 mbar. There are obtained 0.74 g of beige crystals in the polymorph form B, that reveals a powder X-ray diffraction pattern and Raman spectrum, which are identical to those described in example A4.

EXAMPLE A8

Preparation of Polymorph Form B of (6R)-L-erythro-tetrahydrobiopterin dihydrochloride from a Mixture of Hydrate Form C and Ethanol Solvate Form G 60.5 mg hydrate form C according to example B1 and 60.6 mg ethanol solvate form G according to example C1 are suspended in 1.0 ml ethanol (EtOH) under nitrogen. The slurry is stirred over night at room temperature, filtrated and dried in air. Yield: 96.4 mg white crystalline solid, which corresponds to form B according to FT Raman spectrum and X-ray diffraction pattern.

EXAMPLE A9

Preparation of Polymorph Form B of (6R)-L-erythro-tetrahydrobiopterin dihydrochloride from a Mixture of Polymorph Form B and Ethanol Solvate Form G 60.4 mg ethanol solvate form G according to example C1 and 60.3 mg polymorph form B according to example A4 are suspended under nitrogen atmosphere in 1.0 ml ethanol, stirred over night at room temperature, filtrated and then dried in air. Yield: 86.4 mg white crystalline solid, which corresponds to form B according to FT Raman spectrum and X-ray diffraction pattern.

EXAMPLE A10

Preparation of Polymorph Form B of (6R)-L-erythro-tetrahydrobiopterin dihydrochloride from a Mixture of Hydrate form C and Polymorph Form B 60.7 mg polymorph form B according to example A4 and 60.5 mg hydrate form C according to example B1 are suspended under nitrogen in 1.0 ml EtOH. The resulting suspension is stirred over night at room temperature, filtrated and dried in air. Yield: 86.6 mg white, crystalline solid, which corresponds to form B according to FT Raman spectrum and X-ray diffraction pattern.

EXAMPLE A11

Preparation of Polymorph Form B of (6R)-L-erythro-tetrahydrobiopterin dihydrochloride from Polymorph Form A According to Example A1

105 mg of polymorph form A according to example A1 are suspended in 2.0 ml THF containing 2.5% by weight of water. The suspension is stirred at room temperature under nitrogen atmosphere for about 48 hours, filtrated and dried under nitrogen for 20 hours at room temperature. Yield: 91 mg of white, crystalline solid, which corresponds to form B according to FT Raman spectrum and X-ray diffraction pattern.

EXAMPLE A12

Preparation of Polymorph Form B of (6R)-L-erythro-tetrahydrobiopterin dihydrochloride from Hydrate form E according to Example B8

115 mg of hydrate form E according to example B8 are suspended in 1.5 ml EtOH. The suspension is stirred at room temperature under nitrogen atmosphere for about 22 hours, filtrated and dried under nitrogen. Yield: 75 mg of white, crystalline solid, which corresponds to form B according to FT Raman spectrum and X-ray diffraction pattern.

EXAMPLE A13

Preparation of Polymorph form B of (6R)-L-erythro-tetrahydrobiopterin dihydrochloride from Polymorph Form B According to Example A4

205 mg of polymorph form B according to example A4 are suspended in 2.0 ml isopropanol (IPA) containing 5% by weight of water. The suspension is stirred for 24 hours at room temperature, and then filtered and dried under 53% relative humidity in air. Yield: 116 mg of white, crystalline solid, which corresponds to form B according to FT Raman spectrum and X-ray diffraction pattern.

EXAMPLE A14

Preparation of Polymorph Form B of (6R)-L-erythro-tetrahydrobiopterin dihydrochloride from Polymorph form B According to Example A4

205 mg of polymorph form B according to example A4 are suspended in 2.0 ml IPA containing 5% by weight of water. The suspension is stirred for 24 hours at 3° C., then filtered and dried under 53% relative humidity in air. Yield: 145 mg of white, crystalline solid, which corresponds to form B according to FT Raman spectrum and X-ray diffraction pattern.

EXAMPLE A15

Preparation of Polymorph Form B of (6R)-L-erythro-tetrahydrobiopterin dihydrochloride from Polymorph Form A According to Example A1

203 mg polymorph form A according to example A1 are suspended in 2.0 ml IPA and the suspension is stirred at 40° C. for 18 hours, filtered and then dried in air at room temperature. Yield: 192 mg of white, crystalline solid, which corresponds to form B according to FT Raman spectrum and X-ray diffraction pattern.

EXAMPLE A16

Preparation of Polymorph Form B of (6R)-L-erythro-tetrahydrobiopterin dihydrochloride from Polymorph Form B According to Example A4

200 mg polymorph form B according to example A4 are dissolved in 800 μl water. 4.0 ml acetic acid and then 3.0 ml THF added and the resulting suspension is stirred at room temperature for 19 hours. The solid is filtered off and dried in air at room temperature. Yield: 133 mg of white, crystalline solid, which corresponds to form B according to FT Raman spectrum and X-ray diffraction pattern.

EXAMPLE A17

Preparation of Polymorph Form B of (6R)-L-erythro-tetrahydrobiopterin dihydrochloride from Polymorph Form B According to Example A4

256 mg polymorph form B according to example A4 are dissolved in 4.0 ml acetic acid/H2O (4:1) and 4.0 ml acetic acid are added then. The formed suspension is stirred at 20° C. for about 20 hours, filtered and then dried in air for 4 hours. Yield: 173 mg of white, crystalline solid, which corresponds to form B according to FT Raman spectrum and X-ray diffraction pattern.

EXAMPLE A18

Preparation of Polymorph Form B of (6R)-L-erythro-tetrahydrobiopterin dihydrochloride from Acetic Acid Solvate Form I According to Example C7

51 mg of acetic acid solvate form I according to example C7 is suspended in 1.0 ml EtOH and seeded with 7 mg of form B. The suspension is stirred for 20 hours at room temperature, filtered and dried in air at room temperature. Yield: 52 mg of white, crystalline solid, which corresponds to form B according to FT Raman spectrum and X-ray diffraction pattern.

EXAMPLE A19

Preparation of Polymorph Form B of (6R)-L-erythro-tetrahydrobiopterin dihydrochloride from Polymorph Form B According to Example A4

304 mg of polymorph form B according to example A4 are suspended in 10.0 ml acetic acid and 100 μl water are added. The suspension is cooled to 13° C., seeded with 5 mg form B, stirred at 13° C. for 16 hours, filtered and then dried under nitrogen at room temperature. Yield: 276 mg of white, crystalline solid, which corresponds to form B according to FT Raman spectrum and X-ray diffraction pattern.

EXAMPLE A20

Preparation of Polymorph Form B of (6R)-L-erythro-tetrahydrobiopterin dihydrochloride from Polymorph Form B According to Example A4

304 mg of polymorph form B according to example A4 are suspended in 5.0 ml IPA and 100 μl water are added. The suspension is cooled to 3° C., stirred at 3° C. for 16 hours, filtered and dried in air at room temperature. Yield: 272 mg of white, crystalline solid, which corresponds to form B according to FT Raman spectrum and X-ray diffraction pattern.

EXAMPLE A21

Preparation of Polymorph Form B of (6R)-L-erythro-tetrahydrobiopterin dihydrochloride from Polymorph Form B According to Example A4

296 mg polymorph form B according to example A4 are dissolved in 15 ml methanol at 50° C. The solution is cooled to 5° C. and about 9 ml solvent are evaporated. Stirring of the obtained suspension is then continued at 10° C. for 30 minutes. The suspension is filtered and the solid residue is then dried under nitrogen at room temperature. Yield: 122 mg of white, crystalline solid, which corresponds to form B according to FT Raman spectrum and X-ray diffraction pattern.

EXAMPLE A22

Preparation of Polymorph Form B of (6R)-L-erythro-tetrahydrobiopterin dihydrochloride from Polymorph Form K According to Example A28

116 mg of polymorph form K according to example A28 and 7 mg of polymorph form B are suspended in 2.0 ml IPA. The suspension is stirred at 35° C. for about 20 hours, filtered and then dried in air at 40° C. for about 1 hour. Yield: 98 mg of white, crystalline solid, which corresponds to form B according to FT Raman spectrum and X-ray diffraction pattern.

EXAMPLE A23

Preparation of Polymorph Form B of (6R)-L-erythro-tetrahydrobiopterin dihydrochloride from Hydrate Form E According to Example B8

120 mg hydrate form E according to example B8 are suspended in 10 ml EtOH. The obtained suspension is stirred at room temperature for 15 hours, filtered and then dried under nitrogen at room temperature. Yield: 98 mg of white, crystalline solid, which corresponds to form B according to FT Raman spectrum and X-ray diffraction pattern.

EXAMPLE A24

Stability Test of Polymorph Form B of (6R)-L-erythro-tetrahydrobiopterin dihydrochloride a) Storage Stability Polymorph form B of (6R)-L-erythro-tetrahydrobiopterin dihydrochloride is stored during 8 months in a minigrip bag at 40° C. and 75% relative humidity. Purity of the product is determined in different intervals by HPLC. The result is given in table 3.

TABLE 3

| | Starting material | After 1 week | After 1 month | After 3 months | After 8 months |
|---|---|---|---|---|---|
| HPLC (5 area) | 98.4 | 99.4 | 98.3 | 99.1 | 98.1 |

The result demonstrates the unusual and unexpected high storage stability of polymorph form B, which makes it especially suitable for preparation of a stable active substance and processing in the manufacture of formulations and storage stable medicaments.

b) Treatment of Polymorph Form B Under the Following Various Conditions Does Not Effect the Polymorph Form B, Which is Recovered After the Test:

128.2 mg polymorph form B are suspended under nitrogen in 1.0 ml methanol (MeOH). The white suspension is stirred for 5 hours at room temperature, filtrated and dried under nitrogen at room temperature. Yield: 123.4 mg white crystalline solid, polymorph form B.

123.2 mg polymorph form B are suspended under nitrogen in 2.0 ml EtOH. The white suspension is stirred over night at room temperature, filtrated and then dried under nitrogen at room temperature. Yield: 118.6 mg white crystalline solid, polymorph form B.

117.5 mg polymorph form B are suspended under nitrogen in 2.0 ml acetone. The white suspension is stirred over night at room temperature, filtrated and dried under nitrogen room temperature. Yield: 100.3 mg white crystalline solid, polymorph form B.

124.4 mg polymorph form B are suspended under nitrogen in 2.0 ml 2-Propanol. The white suspension is stirred over night at room temperature, filtrated and dried under nitrogen room temperature. Yield: 116.1 mg white crystalline solid, polymorph form B.

100.2 mg polymorph form B are suspended in 2.0 ml EtOH in air. The white suspension is stirred in air over a weekend at room temperature, filtrated and then dried in air at room temperature. Yield: 94.2 mg of slightly yellow crystalline solid, polymorph form B. 119.1 mg of this slightly yellow crystalline solid, polymorph form B are suspended under nitrogen in 1.0 ml THF. The white suspension is stirred for about 20 hours at room temperature, filtrated and dried in air at room temperature. Yield: 114.5 mg of slightly yellow crystalline solid, polymorph form B.

126 mg of polymorph form B are suspended in 2.0 ml acetonitrile containing 2% by weight of water. The suspension is stirred for about 20 hours at room temperature under nitrogen atmosphere, filtrated and then drying under nitrogen. Yield: 116 mg of crystalline white solid, polymorph form B.

122 mg of polymorph form B are suspended in 2.0 ml ethyl acetate containing 2% by weight of water. The suspension is stirred at room temperature under nitrogen atmosphere for about 23 hours, filtrated and dried in air. Yield: 92 mg of crystalline white solid, polymorph form B.

366 mg of polymorph form B are stored in an open container under air at 75% relative humidity at 40° C. for 5 days. The solid is after this storage time at elevated temperature still polymorph form B.

EXAMPLE A25

Preparation of Polymorph Form F of (6R)-L-erythro-tetrahydrobiopterin dihydrochloride from Polymorph Form A According to Example A1

102 mg of polymorph form A according to example A1 are suspended in 1.0 ml IPA. The suspension is stirred at room temperature under nitrogen atmosphere for about 19 hours, filtrated and dried in air. Yield: 102 mg of a crystalline white solid. Investigation of the obtained solid by powder X-ray diffraction and Raman spectroscopy reveals a crystalline form F. TG-FTIR: weight loss between 25-200° C. of 1.3% is attributed to water.

EXAMPLE A26

Preparation of Polymorph Form F of (6R)-L-erythro-tetrahydrobiopterin dihydrochloride from Polymorph Form A According to Example A1

97 mg of polymorph form A according to example A1 are suspended in 2.0 ml IPA. The suspension is stirred at 10° C. for 22 hours, filtered and then dried under nitrogen at room temperature. Yield: 58 mg. The crystalline, white solid is polymorph form F, which shows the powder X-ray diffraction pattern as exhibited in table 4 and in FIG. 6.

TABLE 4

| D-Spacings for form F | | |
|---|---|---|
| Angle [°2θ] | d-spacings [Å] | Intensity (qualitative) |
| 5.2 | 17.1 | vs |
| 7.3 | 12.1 | w |
| 10.3 | 8.6 | w |
| 12.7 | 7.0 | w |
| 13.6 | 6.5 | w |
| 13.9 | 6.4 | w |
| 15.0 | 5.92 | w |
| 15.5 | 5.72 | w |
| 17.4 | 5.11 | w |
| 18.0 | 4.92 | m |
| 18.3 | 4.86 | w |
| 19.0 | 4.68 | m |
| 20.1 | 4.41 | w |
| 21.6 | 4.12 | w |
| 22.9 | 3.88 | w |
| 23.2 | 3.83 | w |
| 24.1 | 3.70 | m |
| 24.5 | 3.64 | w |
| 25.1 | 3.55 | m |
| 25.5 | 3.49 | s |
| 25.8 | 3.46 | s |
| 26.3 | 3.39 | s |
| 26.8 | 3.33 | m |
| 27.0 | 3.31 | m |
| 27.3 | 3.27 | m |
| 27.8 | 3.21 | s |
| 28.0 | 3.19 | m |
| 28.9 | 3.09 | m |
| 29.6 | 3.02 | m |
| 30.2 | 2.96 | m |
| 30.9 | 2.89 | w |
| 31.3 | 2.86 | w |
| 32.0 | 2.80 | m |
| 33.6 | 2.69 | m |

EXAMPLE A27

Preparation of Polymorph Form J of (6R)-L-erythro-tetrahydrobiopterin dihydrochloride from Polymorph Form E According to Example B8

250 mg of form E of (6R)-L-erythro-tetrahydrobiopterin dihydrochloride are dissolved in 5.0 ml acetic acid and 1.0 ml water. To this solution 4.0 ml THF are added and the resulting suspension is slowly cooled to 5° C. Stirring is continued for about 16 hours before the suspension is filtered and obtained crystalline solid is dried under vacuum at ambient temperature. Yield: 179 mg mg of a crystalline white solid. Investigation of the obtained solid by powder X-ray diffraction reveals a crystalline form J, which shows the powder X-ray diffraction pattern as exhibited in table 5 and in FIG. 10. TG-FTIR: weight loss between 25-200° C. of 0.6% is attributed to water.

TABLE 5

| D-Spacing for form J | | |
|---|---|---|
| Angle [°2θ] | d-spacings [Å] | Intensity (qualitative) |
| 6.0 | 14.6 | m |
| 13.4 | 6.6 | w |
| 13.9 | 6.4 | w |
| 16.2 | 5.47 | w |
| 18.3 | 4.84 | w |
| 20.5 | 4.34 | vw |
| 21.2 | 4.20 | vw |
| 21.7 | 4.10 | vw |
| 24.3 | 3.67 | w |
| 25.2 | 3.54 | w |
| 27.1 | 3.29 | vs |
| 27.8 | 3.21 | vs |
| 30.3 | 2.95 | w |
| 31.5 | 2.84 | vw |
| 32.8 | 2.73 | vw |

EXAMPLE A28

Preparation of Polymorph Form K of (6R)-L-erythro-tetrahydrobiopterin dihydrochloride from Polymorph Form B According to Example A4

2.00 g of (6R)-L-erythro-tetrahydrobiopterin dihydrochloride form B and 0.2 g of ascorbic acid are dissolved in 8.0 ml water. Subsequently, 40 ml acetic acid are added to this solution and then 30 ml of THF are slowly added to induce the crystallization. The resulting suspension is cooled to 0° C. and stirring is continued at 0° C. for about one hour before the solid is separated by filtration and washed with about 5 ml of ethanol of 0° C. The obtained crystalline solid is then again suspended in 30 ml ethanol at 0° C. resulting suspension is stirred at 0° C. for about 2 hours before the suspension is filtered and the obtained crystals are washed with 5 ml of ethanol of 0° C. The obtained crystals are dried at 30° C. under reduced pressure (8 mbar) for about 16 hours. Yield: 1.36 g of white crystalline solid. Investigation of the obtained solid by powder X-ray diffraction and Raman spectroscopy reveals a crystalline form K, which shows the powder X-ray diffraction pattern as exhibited in table 6 and in FIG. 11. TG-FTIR: weight loss between 25-200° C. of 0.6% which % is attributed to water.

TABLE 6

| D-Spacing for form K | | |
|---|---|---|
| Angle [°2θ] | d-spacings [Å] | Intensity (qualitative) |
| 6.3 | 14.0 | s |
| 9.4 | 9.4 | w |
| 13.3 | 6.6 | w |
| 13.8 | 6.4 | w |
| 14.0 | 6.3 | w |
| 14.6 | 6.1 | w |
| 14.8 | 6.0 | w |
| 15.7 | 5.66 | w |
| 16.6 | 5.33 | w |
| 17.3 | 5.13 | vw |
| 18.8 | 4.73 | m |
| 19.1 | 4.64 | m |
| 19.8 | 4.48 | w |
| 20.5 | 4.32 | vw |
| 21.1 | 4.22 | w |
| 21.8 | 4.08 | w |
| 22.9 | 3.88 | w |
| 23.5 | 3.79 | w |

TABLE 6-continued

| D-Spacing for form K | | |
|---|---|---|
| Angle [°2θ] | d-spacings [Å] | Intensity (qualitative) |
| 25.2 | 3.54 | m |
| 25.5 | 3.49 | vs |
| 26.3 | 3.39 | m |
| 26.8 | 3.33 | vs |
| 28.5 | 3.13 | s |
| 28.8 | 3.10 | m |
| 29.3 | 3.05 | m |
| 29.7 | 3.01 | m |
| 29.9 | 2.99 | m |
| 30.8 | 2.90 | m |

B) Preparation of Hydrate Forms of (6R)-L-erythro-tetrahydrobiopterin dihydrochloride

EXAMPLE B1

Preparation of Hydrate Form C of (6R)-L-erythro-tetrahydrobiopterin dihydrochloride from Polymorph Form B According to Example A4

116 mg of polymorph form B are suspended in 1.0 ml acetonitrile containing 50 μl water. This suspension is stirred at room temperature for about 22 hours, filtrated and then dried in air at room temperature. Yield: 140 mg of a crystalline white solid, designated as form C. TG-FTIR shows a weight loss of 5.3% between 25 to 200° C., attributed to water and indicating a monohydrate. DSC: melting point near 94° C., ΔH~31 J/g. Investigation of the obtained solid by powder X-ray diffraction reveals a crystalline form C, which shows the powder X-ray diffraction pattern as exhibited in table 7 and in FIG. 3.

TABLE 7

| D-Spacing for form C | | |
|---|---|---|
| Angle [°2θ] | d-spacings [Å] | Intensity (qualitative) |
| 4.9 | 18.2 | m |
| 5.7 | 15.4 | w |
| 6.3 | 13.9 | vs |
| 8.5 | 10.4 | w |
| 9.2 | 9.6 | w |
| 9.4 | 9.4 | vw |
| 9.7 | 9.1 | w |
| 10.1 | 8.8 | m |
| 10.8 | 8.2 | w |
| 11.0 | 8.0 | w |
| 12.9 | 6.8 | m |
| 13.5 | 6.5 | w |
| 14.6 | 6.05 | m |
| 15.4 | 5.77 | w |
| 15.7 | 5.64 | w |
| 16.3 | 5.44 | w |
| 17.1 | 5.19 | w |
| 18.2 | 4.89 | w |
| 18.6 | 4.76 | w |
| 18.9 | 4.70 | w |
| 20.1 | 4.41 | w |
| 20.9 | 4.25 | m |
| 22.2 | 4.00 | m |
| 22.9 | 3.88 | m |
| 23.4 | 3.80 | m |
| 24.8 | 3.59 | s |
| 25.5 | 3.50 | m |
| 25.9 | 3.44 | m |
| 26.4 | 3.37 | m |

TABLE 7-continued

| D-Spacing for form C | | |
|---|---|---|
| Angle [°2θ] | d-spacings [Å] | Intensity (qualitative) |
| 27.3 | 3.26 | s |
| 28.0 | 3.19 | vs |
| 28.1 | 3.17 | s |
| 28.7 | 3.11 | m |
| 29.2 | 3.06 | m |
| 29.6 | 3.02 | m |
| 30.1 | 2.97 | vs |
| 30.6 | 2.93 | m |
| 30.9 | 2.89 | m |
| 31.6 | 2.83 | m |
| 32.6 | 2.75 | w |
| 33.6 | 2.67 | w |
| 34.3 | 2.62 | w |
| 35.0 | 2.56 | w |
| 36.9 | 2.43 | m |

EXAMPLE B2

Stability of hydrate form C of (6R)-L-erythro-tetrahydrobiopterin dihydrochloride 71 mg of hydrate form C according to example B1 are stored under 52% relative humidity and at room temperature for 17 days. Hydrate form C is retained.

EXAMPLE B3

Preparation of Hydrate Form D of (6R)-L-erythro-tetrahydrobiopterin dihydrochloride from Polymorph Form B According to Example A4

A solution of 330 mg polymorph form B according to example A4 in 1.0 ml water is prepared. 600 μl of this solution are added drop-wise to 10.0 ml 2-propanol at room temperature and stirred for about 2 hours. The precipitated solid is filtered off and dried at room temperature in air. Yield: 180 mg of a crystalline, white solid, designated as form D. TG-FTIR shows a weight loss of 4.8% between 25 to 200° C., attributed to water. Karl Fischer titration results in a water content of 6%. DSC: melting point near 153° C., ΔH~111 J/g. Investigation of the obtained solid by powder X-ray diffraction and Raman spectroscopy reveals a crystalline form D, which shows the powder X-ray diffraction pattern as exhibited in table 8 and in FIG. 4.

TABLE 8

| D-Spacing for form D | | |
|---|---|---|
| Angle [°2θ] | d-spacings [Å] | Intensity (qualitative) |
| 9.1 | 9.8 | vw |
| 10.3 | 8.6 | s |
| 13.0 | 6.8 | w |
| 15.2 | 5.84 | vw |
| 16.0 | 5.56 | m |
| 17.8 | 4.99 | m |
| 18.1 | 4.90 | vw |
| 19.0 | 4.67 | s |
| 20.6 | 4.32 | m |
| 21.8 | 4.08 | vw |
| 22.6 | 3.93 | vs |
| 22.9 | 3.88 | w |
| 24.5 | 3.64 | w |
| 26.1 | 3.41 | w |
| 26.6 | 3.36 | vw |
| 27.4 | 3.25 | w |
| 28.2 | 3.17 | m |

TABLE 8-continued

| D-Spacing for form D | | |
|---|---|---|
| Angle [°2θ] | d-spacings [Å] | Intensity (qualitative) |
| 29.3 | 3.05 | s |
| 30.4 | 2.94 | w |
| 30.6 | 2.92 | w |
| 31.0 | 2.88 | m |
| 31.4 | 2.85 | w |
| 31.9 | 2.80 | m |
| 32.1 | 2.79 | m |
| 33.1 | 2.71 | vw |
| 33.4 | 2.68 | w |
| 33.8 | 2.65 | w |
| 34.9 | 2.57 | vw |
| 35.6 | 2.52 | vw |
| 36.13 | 2.49 | vw |
| 37.58 | 2.39 | vw |
| 38.24 | 2.35 | w |
| 38.48 | 2.34 | w |
| 39.12 | 2.30 | w |
| 39.33 | 2.29 | w |

EXAMPLE B4

Preparation of Hydrate Form D of (6R)-L-erythro-tetrahydrobiopterin dihydrochloride from Polymorph Form B According to Example A4

246 mg of polymorph form B according to example A4 are dissolved in 4.0 ml IPA/$H_2O$ (4:1) at 40° C. 4.0 ml IPA are then added and the solution is cooled to 20° C. The formed suspension is stirred for about 20 hours at 20° C. The solid is filtered off and dried in air at room temperature for about 4 hours. A comparison with the crystalline solid of example B3 reveals formation of hydrate form D.

EXAMPLE B5

Preparation of Hydrate Form D of (6R)-L-erythro-tetrahydrobiopterin dihydrochloride from Polymorph Form B According to Example A4

252 mg of polymorph form B according to example A4 are dissolved in 4.0 ml IPA/$H_2O$ (4:1) at 40° C. 4.0 ml IPA are added and the solution is slowly cooled to 5° C. At 25° C. 5 mg of seed crystals of form D are added. The temperature is changed to room temperature. The suspension is stirred for 40 hours, filtered and then dried in air for 5 hours at room temperature. A comparison with the crystalline solid of example B3 reveals formation of hydrate form D.

EXAMPLE B6

Preparation of Hydrate Form D of (6R)-L-erythro-tetrahydrobiopterin dihydrochloride from Hydrate Form C According to Example B1

700 mg of from hydrate form C according to example B1 are suspended in IPA/$H_2O$ (9:1). The suspension is stirred for 5 hours at room temperature, filtered and the solid dried in air at room temperature. Yield: 470 mg of white, crystalline solid, corresponding to hydrate form D.

EXAMPLE B7

Treatment of Hydrate Form D of (6R)-L-erythro-tetrahydrobiopterin dihydrochloride in Isopropanol 105 mg of hydrate form D according to example B3 are suspended in 2.0 ml IPA. The suspension is stirred at room temperature for about 18 hours, filtered and the solid then dried in air at room temperature for about 4 hours. The obtained solid is the unchanged hydrate form D.

EXAMPLE B8

Preparation of Hydrate Form E of (6R)-L-erythro-tetrahydrobiopterin dihydrochloride from Polymorph Form B According to Example A4

489 mg of polymorph form B according to example A4 are dissolved in 1.0 ml water. The aqueous solution is added at 5° C. to 20 ml THF. The formed suspension is stirred for about 20 hours at 5° C., filtrated and dried under nitrogen at room temperature. Yield: 486 mg of a crystalline, pale yellow solid, designated as form E. TG-FTIR shows a weight loss of 10.8% between 25 to 200° C., attributed to water. Karl Fischer titration results in a water content of 11.0%, which suggests a dihydrate. Investigation of the obtained solid by powder X-ray diffraction reveals a crystalline form E, which shows the powder X-ray diffraction pattern as exhibited in table 9 and in FIG. 5.

TABLE 9

| D-Spacing for form E | | |
|---|---|---|
| Angle [°2θ] | d-spacings [Å] | Intensity (qualitative) |
| 5.7 | 15.4 | s |
| 13.3 | 6.6 | w |
| 13.7 | 6.5 | w |
| 14.9 | 5.95 | vw |
| 15.8 | 5.61 | vw |
| 16.2 | 5.48 | w |
| 16.9 | 5.24 | w |
| 18.2 | 4.87 | w |
| 19.7 | 4.50 | vw |
| 20.8 | 4.27 | w |
| 22.6 | 3.94 | w |
| 23.6 | 3.78 | w |
| 24.1 | 3.69 | m |
| 24.8 | 3.60 | w |
| 26.0 | 3.43 | w |
| 26.8 | 3.33 | s |
| 27.4 | 3.26 | vs |
| 28.3 | 3.16 | w |
| 29.0 | 3.08 | m |
| 29.6 | 3.02 | w |
| 29.9 | 2.98 | w |
| 30.3 | 2.95 | m |
| 30.7 | 2.91 | w |
| 31.1 | 2.87 | m |
| 32.0 | 2.79 | w |
| 32.7 | 2.74 | w |
| 33.2 | 2.69 | w |
| 34.2 | 2.62 | w |

EXAMPLE B9

Preparation of Hydrate Form E of (6R)-L-erythro-tetrahydrobiopterin dihydrochloride from Polymorph Form B According to Example A4

10 ml THF are cooled to 5° C. and then 400 μl of a concentrated aqueous solution containing about 160 mg polymorph form B according to example A4 is added drop-wise under stirring. The resulting suspension is stirred at 5° C. for about 2 hours at 5° C., then the precipitated solid is filtered off and dried in air at room temperature. Yield: 123.2 mg pale yellow crystalline solid, corresponding to hydrate form E.

EXAMPLE B10

Preparation of Hydrate Form E of (6R)-L-erythro-tetrahydrobiopterin dihydrochloride from Polymorph Form B According to Example A4

306 mg of polymorph form B according to example A4 are dissolved in 1.5 ml water. The water is evaporated from the aqueous solution under nitrogen at room temperature to dryness. The pale yellow crystalline residue corresponds to hydrate form E.

EXAMPLE B11

Preparation of Hydrate form E of (6R)-L-erythro-tetrahydrobiopterin dihydrochloride from Polymorph form A According to Example A1

71 mg of polymorph form A according to example A1 are stored in air under 52% relative humidity at room temperature for 17 days. The obtained pale yellow crystalline solid corresponds to hydrate form E. Hydrate form E is retained, when this solid is are stored in air under 52% relative humidity at room temperature for 17 days.

EXAMPLE B12

Preparation of Hydrate Form E of (6R)-L-erythro-tetrahydrobiopterin dihydrochloride from Polymorph Form B According to Example A4

200 mg of polymorph form B according to example A4 are dissolved in 800 μl water. 4.0 ml acetic acid and then 3.0 ml THF are added the solution. The suspension is stirred at 0° C. for 19 hours, the solid filtered off and dried in air at room temperature. Yield: 159 mg pale yellow crystalline solid corresponding to hydrate form E.

EXAMPLE B13

Preparation of Hydrate Form H of (6R)-L-erythro-tetrahydrobiopterin dihydrochloride from Polymorph Form B According to Example A4

250 mg of polymorph form B according to example A4 are dissolved in a mixture of 5.0 ml acetic acid and 1.0 ml water. To this solution are added 10 ml of THF as non-solvent. The obtained suspension is cooled to 0° C. and then stirred for 18 hours at 0° C. After addition of THF the void volume of the glass vial is purged with nitrogen and the cap is closed. The solid is filtered off and dried 24 hours room temperature under vacuum. Yield: 231 mg of a crystalline, pale yellow solid, designated as form H. TG-FTIR shows a weight loss of 6.5% between 25 to 200° C., attributed to water. Karl Fischer titration results in a water content of 6.34%. Investigation of the obtained solid by powder X-ray diffraction reveals a crystalline form H, which shows the powder X-ray diffraction pattern as exhibited in table 10 and in FIG. 8.

TABLE 10

D-Spacing for form H

| Angle [°2θ] | d-spacings [Å] | Intensity (qualitative) |
|---|---|---|
| 5.6 | 15.8 | vs |
| 8.6 | 10.3 | vw |
| 11.0 | 8.0 | vw |
| 13.4 | 6.6 | vw |
| 14.6 | 6.07 | vw |
| 18.5 | 4.81 | vw |
| 20.6 | 4.30 | vw |
| 23.0 | 3.87 | w |
| 24.7 | 3.60 | w |
| 27.3 | 3.27 | w |
| 27.8 | 3.21 | m |
| 28.5 | 3.13 | vw |
| 29.3 | 3.05 | vw |
| 30.2 | 2.96 | w |
| 31.0 | 2.89 | w |
| 31.8 | 2.82 | vw |
| 33.5 | 2.67 | m |

EXAMPLE B14

Preparation of Hydrate Form O of (6R)-L-erythro-tetrahydrobiopterin dihydrochloride from Polymorph Form F According to Example A26

About 50 mg of polymorph form F according to example A26 are placed on an powder X-ray diffraction sample holder of 0.8 mm thickness (TTK type, obtained form Anton Paar GmbH, Graz, Austria). The prepared sample holder is placed in the closed sample chamber of a Philips X'Pert powder X-ray diffractometer and the sample chamber is purged with nitrogen and partially saturated with water vapour to a resulting relative humidity of about 52%. After an exposure time of about 24 hour a powder X-ray diffraction pattern is recorded. Investigation of the obtained solid sample by powder X-ray diffraction reveals a crystalline form O, which shows the powder X-ray diffraction pattern as exhibited in table 11 and in FIG. 15.

TABLE 11

D-Spacing for form O

| Angle [°2θ] | d-spacings [Å] | Intensity (qualitative) |
|---|---|---|
| 5.5 | 15.9 | w |
| 6.3 | 14.0 | w |
| 7.4 | 12.0 | w |
| 10.0 | 8.8 | m |
| 12.6 | 7.0 | w |
| 13.6 | 6.5 | w |
| 14.1 | 6.3 | m |
| 14.8 | 6.00 | w |
| 15.4 | 5.75 | w |
| 15.7 | 5.65 | m |
| 17.5 | 5.06 | m |
| 17.8 | 4.98 | m |
| 18.0 | 4.92 | m |
| 18.3 | 4.84 | w |
| 18.6 | 4.77 | w |
| 20.1 | 4.42 | w |
| 20.5 | 4.33 | w |

TABLE 11-continued

| D-Spacing for form O | | |
|---|---|---|
| Angle [°2θ] | d-spacings [Å] | Intensity (qualitative) |
| 22.2 | 4.00 | m |
| 22.9 | 3.88 | m |
| 23.5 | 3.78 | w |
| 24.1 | 3.69 | s |
| 24.5 | 3.64 | s |
| 25.3 | 3.52 | vs |
| 25.5 | 3.49 | s |
| 25.8 | 3.46 | s |
| 26.1 | 3.42 | s |
| 26.8 | 3.32 | m |
| 27.3 | 3.27 | m |
| 27.6 | 3.23 | s |
| 28.0 | 3.18 | s |
| 28.3 | 3.15 | vs |
| 28.6 | 3.12 | m |
| 29.4 | 3.04 | vs |
| 30.3 | 2.95 | m |
| 31.8 | 2.81 | s |
| 32.9 | 2.72 | m |
| 33.6 | 2.67 | m |
| 34.3 | 2.61 | m |

C) Preparation of Solvate Forms of (6R)-L-erythro-tetrahydrobiopterin dihydrochloride

EXAMPLE C1

Preparation of Form G of (6R)-L-erythro-tetrahydrobiopterin dihydrochloride from Polymorph Form B According to Example A4

245 mg of polymorph form B according to example A4 are suspended in 4.0 ml ethanol. 0.5 ml water are added and the mixture is heated to 70° C. to dissolve form B. The solution is cooled to 10° C. 2 ml of ethanol are added and the formed suspension is stirred for about 4 hours at 10° C. The solid is filtered off and dried for about 30 minutes under a slight flow of nitrogen at room temperature. Yield: 190 mg of crystalline white solid designated as form G. TG-FTIR shows a weight loss of 11.5% between 25 to 200° C., which is attributed to loss of ethanol and suggests an ethanol solvate. Investigation of the obtained solid by powder X-ray diffraction reveals a crystalline form G, which shows the powder X-ray diffraction pattern as exhibited in table 12 and in FIG. 7.

TABLE 12

| D-Spacing for form G | | |
|---|---|---|
| Angle [°2θ] | d-spacings [Å] | Intensity (qualitative) |
| 6.1 | 14.5 | vs |
| 8.1 | 10.9 | w |
| 9.0 | 9.8 | w |
| 12.7 | 7.0 | w |
| 14.1 | 6.3 | w |
| 15.4 | 5.74 | w |
| 16.9 | 5.24 | vw |
| 17.6 | 5.04 | vw |
| 18.5 | 4.79 | w |
| 20.1 | 4.41 | w |
| 22.1 | 4.02 | w |
| 23.0 | 3.86 | w |
| 23.6 | 3.77 | w |
| 24.1 | 3.69 | w |
| 24.6 | 3.63 | m |
| 25.0 | 3.57 | m |
| 25.5 | 3.49 | m |
| 26.2 | 3.41 | m |
| 27.3 | 3.26 | m |
| 28.1 | 3.17 | m |
| 29.0 | 3.07 | m |
| 30.1 | 2.97 | m |
| 30.3 | 2.95 | m |
| 31.2 | 2.87 | w |
| 34.3 | 2.61 | w |

EXAMPLE C2

Preparation of Form G of (6R)-L-erythro-tetrahydrobiopterin dihydrochloride from Polymorph Form B According to Example A4

200 mg of polymorph form B according to example A4 are dissolved in 400 μl water then precipitated with the addition of 10 ml ethanol. A precipitate is formed and the suspension is stirred for 17 hours at 0° C. The solid is filtered off and dried in air at room temperature for about 1 hour. Yield: 161 mg of crystalline white solid corresponding to ethanol solvate G according to example C1.

EXAMPLE C3

Preparation of Form L of (6R)-L-erythro-tetrahydrobiopterin dihydrochloride from Hydrate Form E According to Example B8

104 mg of hydrate form E according to example B8 are suspended in ethanol and the suspension is stirred at 4° C. for about 16 hours. The solid is filtered off and dried under nitrogen at room temperature. Yield: 100 mg of crystalline white solid designated as form L. TG-FTIR shows a weight loss of 9.1% between 25 to 200° C., which is attributed to ethanol and water. This weight loss suggests a mixed water/ethanol solvate. Investigation of the obtained solid by powder X-ray diffraction reveals a crystalline form L, which shows the powder X-ray diffraction pattern as exhibited in table 13 and in FIG. 12.

TABLE 13

| D-Spacing for form L | | |
|---|---|---|
| Angle [°2θ] | d-spacings [Å] | Intensity (qualitative) |
| 6.3 | 14.1 | vs |
| 8.5 | 10.4 | w |
| 9.3 | 9.5 | w |
| 9.8 | 9.0 | vw |
| 12.9 | 6.9 | w |
| 13.6 | 6.5 | w |
| 14.4 | 6.1 | w |
| 15.4 | 5.75 | w |
| 15.8 | 5.61 | w |
| 17.5 | 5.08 | w |
| 18.9 | 4.71 | w |
| 23.1 | 3.86 | w |
| 23.5 | 3.78 | w |
| 25.7 | 3.46 | m |
| 26.5 | 3.36 | m |
| 29.2 | 3.06 | w |
| 30.8 | 2.90 | w |
| 31.8 | 2.82 | w |

EXAMPLE C4

Preparation of Form L of (6R)-L-erythro-tetrahydrobiopterin dihydrochloride from Form B According to Example A4

2.0 g of form B according to example A4 are dissolved in 3.0 ml of water. This solution is slowly added to 70 ml absolute ethanol (not denaturated) at room temperature. Approximately 300 mg of ascorbic acid are added to the aqueous solution and the void volume of the suspension is purged with nitrogen to prevent oxidation. The resulting suspension is cooled to 0° C. and stirred at this temperature for about three hours. Thereafter the suspension is filtered and the solid residue is washed with 6.0 g ethanol and dried for 18 hours at 35° C. under reduced pressure (8 mbar). Yield: 1.41 g. TG-FTIR shows a weight loss of 3.0% between 25 to 200° C., attributed to water. This results suggests that form L can exist either in form of an ethanol solvate, or in form of mixed ethanol solvate/hydrate, or as an non-solvated form containing as small amount of water. The solid residue comprises form L as shown by a comparison of powder X-ray diffraction pattern with that in example.

EXAMPLE C5

Preparation of Form M of (6R)-L-erythro-tetrahydrobiopterin dihydrochloride from Polymorph Form B According to Example A4

120 mg of form B of (6R)-L-erythro-tetrahydrobiopterin dihydrochloride according to example A4 are dissolved in 100 ml of absolute ethanol at 40° C. This solution is evaporated to dryness under a slight flow of nitrogen. The obtained crystalline white solid is designated as form M. TG-FTIR shows a weight loss of 9.1% between 25 to 200° C., attributed to ethanol and water, suggesting a mixed water/ethanol solvate. Investigation of the obtained solid by powder X-ray diffraction reveals a crystalline form M, which shows the powder X-ray diffraction pattern as exhibited in table 14 and in FIG. 13.

TABLE 14

D-Spacing for form M

| Angle [°2θ] | d-spacings [Å] | Intensity (qualitative) |
|---|---|---|
| 4.7 | 18.9 | s |
| 13.9 | 6.4 | m |
| 14.6 | 6.06 | w |
| 15.7 | 5.66 | w |
| 16.8 | 5.28 | w |
| 19.7 | 4.50 | w |
| 21.0 | 4.23 | w |
| 27.7 | 3.22 | vs |

EXAMPLE C6

Preparation of Form N of (6R)-L-erythro-tetrahydrobiopterin dihydrochloride from Ethanol Solvate Form B According to Example A4

250 mg of form B according to example A4 are dissolved in 4.0 ml of a mixture of isopropanol and water (4:1). To this solution 4.0 ml of IPA are slowly added and the resulting suspension is cooled to 0° C. and stirred for about 18 hours at this temperature. The suspension is filtered and the solid residue washed with 4 ml of isopropanol at room temperature. The obtained crystalline material is then dried at 30° C. und reduced pressure (8 mbar) for about 18 hours. Yield: 150 mg. TG-FTIR shows a weight loss of 9.0% between 25 to 200° C., which is attributed to both isopropanol and water. This result suggests that form N can exist either in form of an isopropanol solvate, or in form of mixed isopropanol solvate/hydrate, or as an non-solvated form containing a small amount of water. Investigation by powder X-ray diffraction shows that the solid residue comprises form N, which shows the powder X-ray diffraction pattern as exhibited in table 15 and in FIG. 14.

TABLE 15

D-Spacing for form N

| Angle [°2θ] | d-spacings [Å] | Intensity (qualitative) |
|---|---|---|
| 4.5 | 19.5 | m |
| 8.9 | 9.9 | w |
| 13.3 | 6.7 | w |
| 17.2 | 5.15 | w |
| 18.4 | 4.83 | w |
| 22.7 | 3.91 | w |
| 25.0 | 3.56 | m |
| 26.8 | 3.33 | vs |
| 28.3 | 3.15 | w |
| 30.9 | 2.89 | w |
| 31.9 | 2.81 | w |
| 35.1 | 2.56 | w |
| 38.2 | 2.36 | w |

EXAMPLE C7

Preparation of Acetic Acid Solvate Form I of (6R)-L-erythro-tetrahydrobiopterin dihydrochloride From Polymorph Form B According to Example A4

252 mg of polymorph form B according to example A4 are dissolved at 40° C. in 4.0 ml acetic acid/water (4:1). 4.0 ml acetic are then added acid and the solution is cooled to 5° C. The resulting suspension is stirred for 66 hours. The solid is filtered off and dried in air for 5 hours at room temperature. Yield: 190 mg of crystalline white solid designated as form I. TG-FTIR reveals that form I contains about 12.7% by weight of acetic acid, which suggests an acetic acid solvate. Investigation of the obtained solid by powder X-ray diffraction reveals a crystalline form I, which shows the powder X-ray diffraction pattern as exhibited in table 16 and in FIG. 9.

TABLE 16

D-Spacing for form I

| Angle [°2θ] | d-spacings [Å] | Intensity (qualitative) |
|---|---|---|
| 6.1 | 14.5 | m |
| 6.3 | 14.0 | w |
| 8.1 | 11.0 | w |
| 12.7 | 7.0 | vw |
| 12.9 | 6.9 | vw |
| 14.3 | 6.2 | vw |
| 16.7 | 5.30 | w |
| 18.5 | 4.79 | w |
| 20.0 | 4.44 | w |
| 20.7 | 4.29 | w |
| 21.2 | 4.20 | vw |
| 21.8 | 4.07 | vw |
| 22.1 | 4.02 | w |
| 23.2 | 3.84 | w |

TABLE 16-continued

| D-Spacing for form I | | |
|---|---|---|
| Angle [°2θ] | d-spacings [Å] | Intensity (qualitative) |
| 23.4 | 3.80 | w |
| 24.2 | 3.67 | vs |
| 24.7 | 3.61 | m |
| 25.0 | 3.56 | w |
| 25.9 | 3.44 | m |
| 27.3 | 3.27 | w |
| 27.9 | 3.19 | w |
| 28.8 | 3.11 | s |
| 29.8 | 3.00 | m |
| 30.4 | 2.94 | w |
| 31.2 | 2.87 | w |
| 32.0 | 2.80 | w |

EXPERIMENTAL

Powder X-ray Diffraction (PXRD): PXRD is performed either on a Philips 1710 or on a Philips X'Pert powder X-ray diffractometer using $Cu_{K\alpha}$ radiation. D-spacings are calculated from the 2θ using the wavelength of the $Cu_{K\alpha 1}$ radiation of 1.54060 A. The X-ray tube was operated at a Voltage of 45 kV (or 40 kV with X'Pert Instrument), and a current of 45 mA (or 40 mA with X'Pert Instrument). A step size of 0.02°, and a counting time of 2.4 s per step is applied. Generally, 2θ values are within an error of ±0.1-0.2°. The experimental error on the d-spacing values is therefore dependent on the peak location.

TG-FTIR: Thermogravimetric measurements are carried out with a Netzsch Thermo-Microbalance TG 209 coupled to a Bruker FTIR Spectrometer Vector 22 (sample pans with a pinhole, $N_2$ atmosphere, heating rate 10 K/min).

Raman spectroscopy: FT-Raman spectra are recorded on a Bruker RFS 100 FT-Raman system with a near infrared Nd:YAG laser operating at 1064 nm and a liquid nitrogen-cooled germanium detector. For each sample, 64 scans with a resolution of 2 $cm^{-1}$ are accumulated. Generally, 300 mW laser power is used.

Figure 1:
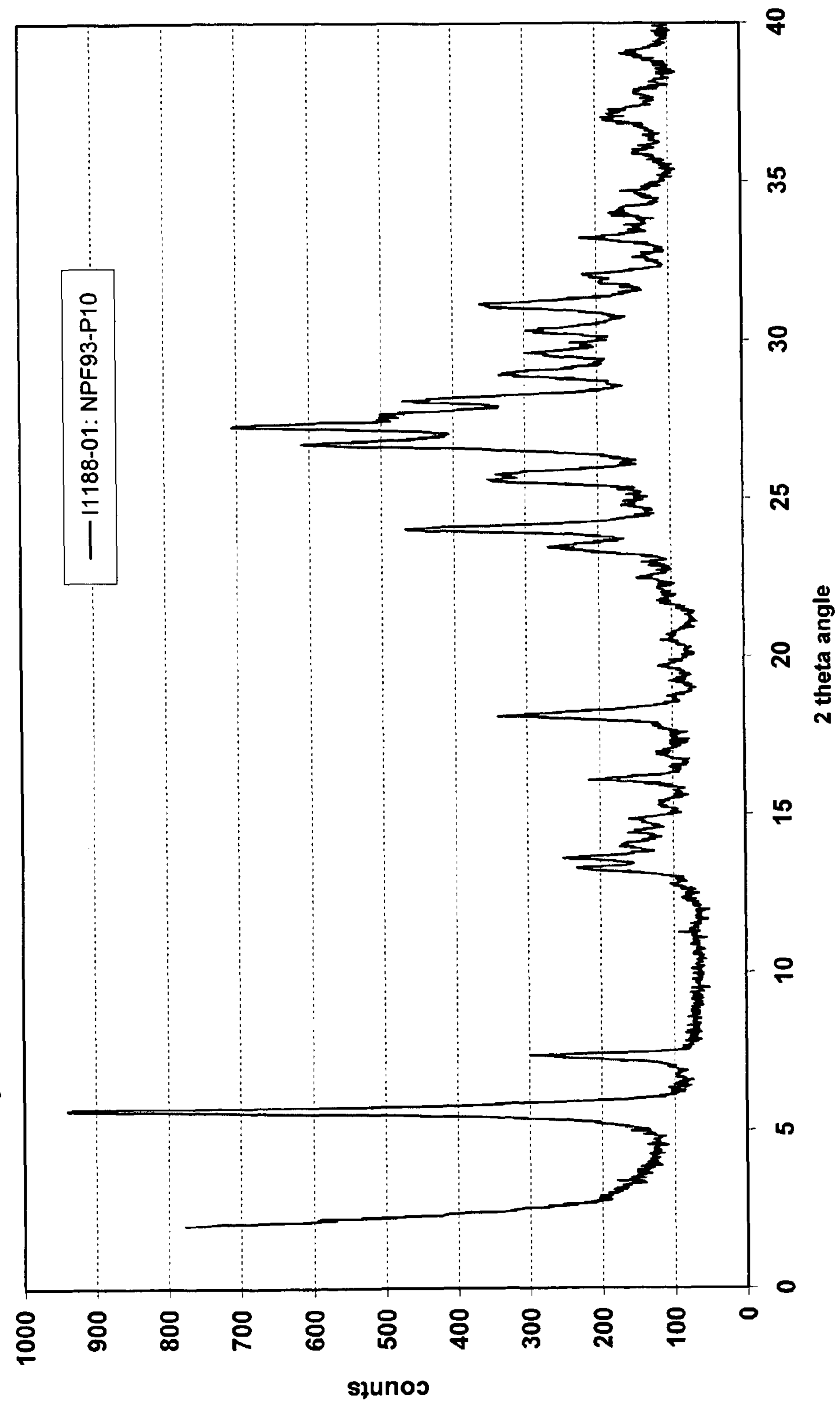
FIG. 1 is a characteristic X-ray powder diffraction pattern for form A

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and, all parts and percentages are by weight, unless otherwise indicated.

The entire disclosure of all applications, patents and publications, cited herein and of corresponding U.S. Provisional Application Ser. No. 60/520,377, filed Nov. 17, 2003 is incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A crystalline form of (6R)-L-erythro-tetrahydrobiopterin dihydrochloride, which exhibits a characteristic X-ray powder diffraction pattern with characteristic peaks expressed in d-values (Å):

for form A, which is a crystalline polymorph:

15.5 (vs), 12.0 (m), 4.89 (m), 3.70 (s), 3.33 (s), 3.26 (s), and 3.18 (m); or for form F, which is a crystalline polymorph:

17.1 (vs), 4.92 (m), 4.68 (m), 3.49 (s), 3.46 (vs), 3.39 (s), 3.21 (m), and 3.19 (m); or for form J, which is a crystalline polymorph:

14.6 (m), 3.29 (vs), and 3.21 (vs); or for form K, which is a crystalline polymorph:

14.0 (s), 6.6 (w), 4.73 (m), 4.64 (m), 3.54 (m), 3.49 (vs), 3.39 (m), 3.33 (vs), 3.13 (s), 3.10 (m), 3.05 (m), 3.01 (m), 2.99 (m), and 2.90 (m); or for form C, which is a crystalline hydrate:

13.9 (vs), 8.8 (m), 6.8 (m), 6.05 (m), 4.25 (m), 4.00 (m), 3.88 (m), 3.80 (m), 3.59 (s), 3.50 (m), 3.44 (m), 3.26 (s), 3.19 (vs), 3.17 (s), 3.11 (m), 2.97 (m), and 2.93 (vs); or for form D, which is a crystalline hydrate:

8.6 (s), 5.56 (m), 4.99 (m), 4.67 (s), 4.32 (m), 3.93 (vs), 3.17 (m), 3.05 (s), 2.88 (m), and 2.79 (m); or for form E, which is a crystalline hydrate:

15.4 (s), 4.87 (w), 3.69 (m), 3.33 (s), 3.26 (vs), 3.08 (m), 2.95 (m), and 2.87 (m); or for form H, which is a crystalline hydrate:

15.8 (vs), 3.87 (m), 3.60 (m), 3.27 (m), 3.21 (m), 2.96 (m), 2.89 (m), and 2.67 (m); or for form O, which is a crystalline hydrate:

8.8 (m), 6.3 (m), 5.65 (m), 5.06 (m), 4.00 (m), 3.88 (m), 3.69 (s), 3.64 (s), 3.52 (vs), 3.49 (s), 3.46 (s), 3.42 (s), 3.32 (m), 3.27 (m), 3.23 (s), 3.18 (s), 3.15 (vs), 3.12 (m), and 3.04 (vs); or for form G, which is a crystalline ethanol solvate:

14.5 (vs), 7.0 (w), 4.41 (w), 3.63 (m), 3.57 (m), 3.49 (w), 3.41 (m), 3.26 (m), 3.17 (m), 3.07 (m), 2.97 (m), 2.95 (m), 2.87 (w), and 2.61 (w); or for form I, which is a crystalline acetic acid solvate:

14.5 (m), 3.67 (vs), 3.61 (m), 3.44 (m), 3.11 (s), and 3.00 (m); or for form L, which is a crystalline mixed ethanol solvate/hydrate:

14.1 (vs), 10.4 (w), 6.9 (w), 6.5 (w), 6.1 (w), 4.71 (w), 3.46 (m), 3.36 (m), and 2.82 (w); or for form M, which is a crystalline ethanol solvate:

18.9 (s), 6.4 (m), and 3.22 (vs); or for form N, which is a crystalline polymorph:

19.5 (m), 6.7 (w), 3.56 (m), and 3.33 (vs), 3.15 (w).

2. A crystalline form of (6R)-L-erythro-tetrahydrobiopterin dihydrochloride according to claim 1, which exhibits a characteristic X-ray powder diffraction pattern with characteristic peaks expressed in d-values (Å)

for form A:

15.5 (vs), 12.0 (m), 6.7 (m), 6.5 (m), 6.3 (w), 6.1 (w), 5.96 (w), 5.49 (m), 4.89 (m), 3.79 (m), 3.70 (s), 3.48 (m), 3.45 (m), 3.33 (s), 3.26 (s), 3.22 (m), 3.18 (m), 3.08 (m), 3.02 (w), 2.95 (w), 2.87 (m), 2.79 (w), 2.70 (w); or for form F:

17.1 (vs), 12.1 (w), 8.6 (w), 7.0 (w), 6.5 (w), 6.4 (w), 5.92 (w), 5.72 (w), 5.11 (w), 4.92 (m), 4.86 (w), 4.68 (m), 4.41 (w), 4.12 (w), 3.88 (w), 3.83 (w), 3.70 (m), 3.64 (w), 3.55 (m), 3.49 (s), 3.46 (vs), 3.39 (s), 3.33 (m), 3.31 (m), 3.27 (m), 3.21 (m), 3.19 (m), 3.09 (m), 3.02 (m), and 2.96 (m); or for form J:

14.6 (m), 6.6 (w), 6.4 (w), 5.47 (w), 4.84 (w), 3.29 (vs), and 3.21 (vs); or for form K:

14.0 (s), 9.4 (w), 6.6 (w), 6.4 (w), 6.3 (w), 6.1 (w), 6.0 (w), 5.66 (w), 5.33 (w), 5.13 (vw), 4.73 (m), 4.64 (m), 4.48 (w), 4.32 (vw), 4.22 (w), 4.08 (w), 3.88 (w), 3.79 (w), 3.54 (m), 3.49 (vs), 3.39 (m), 3.33 (vs), 3.13 (s), 3.10 (m), 3.05 (m), 3.01 (m), 2.99 (m), and 2.90 (m); or for form C:

18.2 (m), 15.4 (w), 13.9 (vs), 10.4 (w), 9.6 (w), 9.1 (w), 8.8 (m), 8.2 (w), 8.0 (w), 6.8 (m), 6.5 (w), 6.05 (m), 5.77 (w), 5.64 (w), 5.44 (w), 5.19 (w), 4.89 (w), 4.76 (w), 4.70 (w), 4.41 (w), 4.25 (m), 4.00 (m), 3.88 (m), 3.80 (m), 3.59 (s), 3.50 (m), 3.44 (m), 3.37 (m), 3.26 (s), 3.19 (vs), 3.17 (s), 3.11 (m), 3.06 (m), 3.02 (m), 2.97 (vs), 2.93 (m), 2.89 (m), 2.83 (m), and 2.43 (m); or for form D:

8.6 (s), 6.8 (w), 5.56 (m), 4.99 (m), 4.67 (s), 4.32 (m), 3.93 (vs), 3.88 (w), 3.64 (w), 3.41 (w), 3.25 (w), 3.17 (m), 3.05 (s), 2.94 (w), 2.92 (w), 2.88 (m), 2.85 (w), 2.80 (w), 2.79 (m), 2.68 (w), 2.65 (w), 2.52 (vw), 2.35 (w), 2.34 (w), 2.30 (w), and 2.29 (w); or for form E:

15.4 (s), 6.6 (w), 6.5 (w), 5.95 (vw), 5.61 (vw), 5.48 (w), 5.24 (w), 4.87 (w), 4.50 (vw), 4.27 (w), 3.94 (w), 3.78 (w), 3.69 (m), 3.60 (w), 3.33 (s), 3.26 (vs), 3.16 (w), 3.08 (m), 2.98 (w), 2.95 (m), 2.91 (w), 2.87 (m), 2.79 (w), 2.74 (w), 2.69 (w), and 2.62 (w); or for form H:

15.8 (vs), 10.3 (w), 8.0 (w), 6.6 (w), 6.07 (w), 4.81 (w), 4.30 (w), 3.87 (m), 3.60 (m), 3.27 (m), 3.21 (m), 3.13 (w), 3.05 (w), 2.96 (m), 2.89 (m), 2.82 (w), and 2.67 (m); or for form O:

15.9 (w), 14.0 (w), 12.0 (w), 8.8 (m), 7.0 (w), 6.5 (w), 6.3 (m), 6.00 (w), 5.75 (w), 5.65 (m), 5.06 (m), 4.98 (m), 4.92 (m), 4.84 (w), 4.77 (w), 4.42 (w), 4.33 (w), 4.00 (m), 3.88 (m), 3.78 (w), 3.69 (s), 3.64 (s), 3.52 (vs), 3.49 (s), 3.46 (s), 3.42 (s), 3.32 (m), 3.27 (m), 3.23 (s), 3.18 (s), 3.15 (vs), 3.12 (m), 3.04 (vs), 2.95 (m), 2.81 (s), 2.72 (m), 2.67 (m), and 2.61 (m); or for form G:

14.5 (vs), 10.9 (w), 9.8 (w), 7.0 (w), 6.3 (w), 5.74 (w), 5.24 (vw), 5.04 (vw), 4.79 (w), 4.41 (w), 4.02 (w), 3.86 (w), 3.77 (w), 3.69 (w), 3.63 (m), 3.57 (m), 3.49 (m), 3.41 (m), 3.26 (m), 3.17 (m), 3.07 (m), 2.97 (m), 2.95 (m), 2.87 (w), and 2.61 (w); or for form I:

14.5 (m), 14.0 (w), 11.0 (w), 7.0 (vw), 6.9 (vw), 6.2 (vw), 5.30 (w), 4.79 (w), 4.44 (w), 4.29 (w), 4.20 (vw), 4.02 (w), 3.84 (w), 3.80 (w), 3.67 (vs), 3.61 (m), 3.56 (w), 3.44 (m), 3.27 (w), 3.19 (w), 3.11 (s), 3.00 (m), 2.94 (w), 2.87 (w), and 2.80 (w); or for form L:

14.1 (vs), 10.4 (w), 9.5 (w), 9.0 (vw), 6.9 (w), 6.5 (w), 6.1 (w), 5.75 (w), 5.61 (w), 5.08 (w), 4.71 (w), 3.86 (w), 3.78 (w), 3.46 (m), 3.36 (m), 3.06 (w), 2.90 (w), and 2.82 (w); or for form M:

18.9 (s), 6.4 (m), 6.06 (w), 5.66 (w), 5.28 (w), 4.50 (w), 4.23 (w), and 3.22 (vs); or for form N:

19.5 (m), 9.9 (w), 6.7 (w), 5.15 (w), 4.83 (w), 3.91 (w), 3.56 (m), 3.33 (vs), 3.15 (w), 2.89 (w), 2.81 (w), 2.56 (w), and 2.36 (w).

Figure 3:
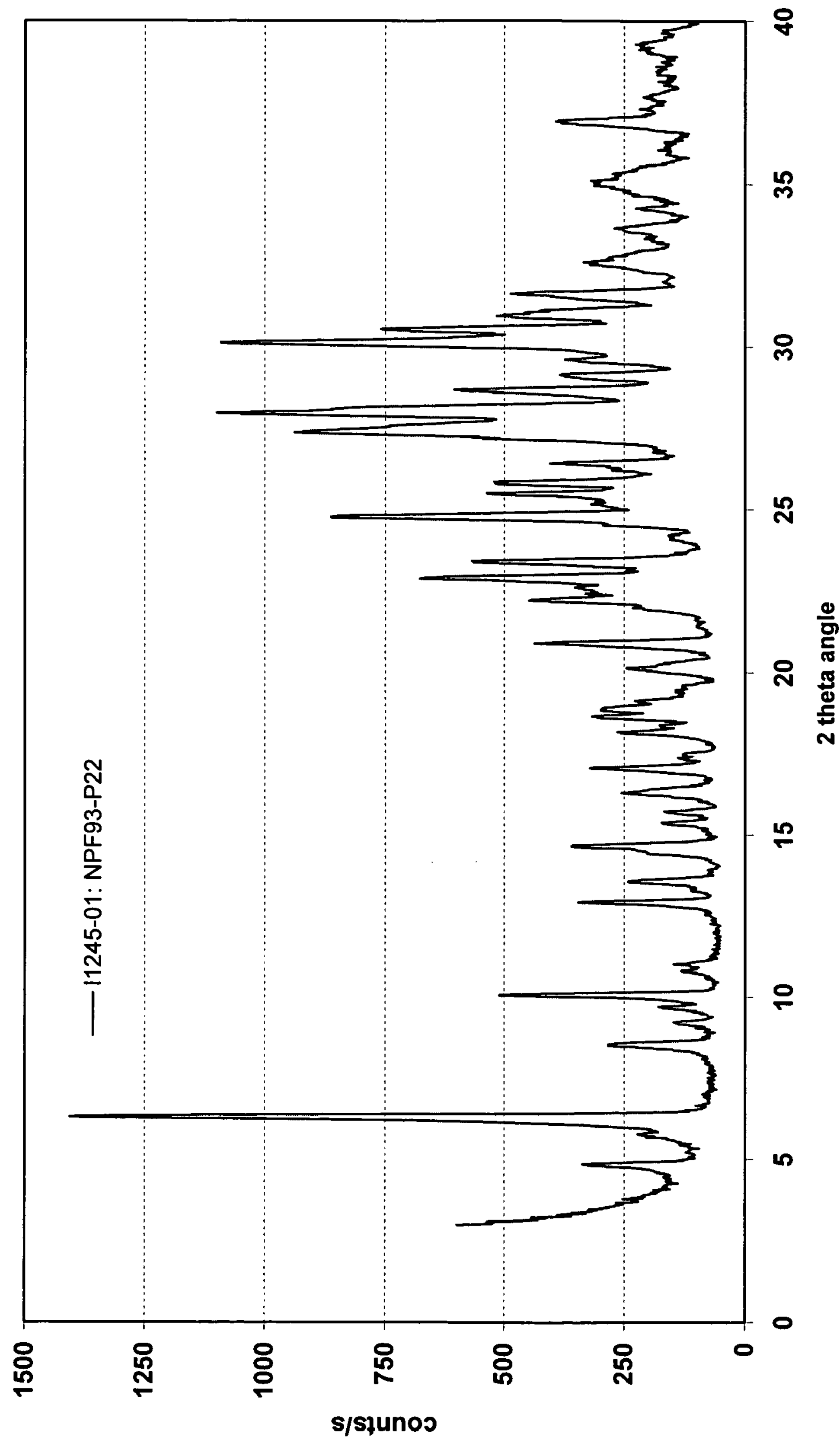
FIG. 3 is a characteristic X-ray powder diffraction pattern for form C
Figure 4:
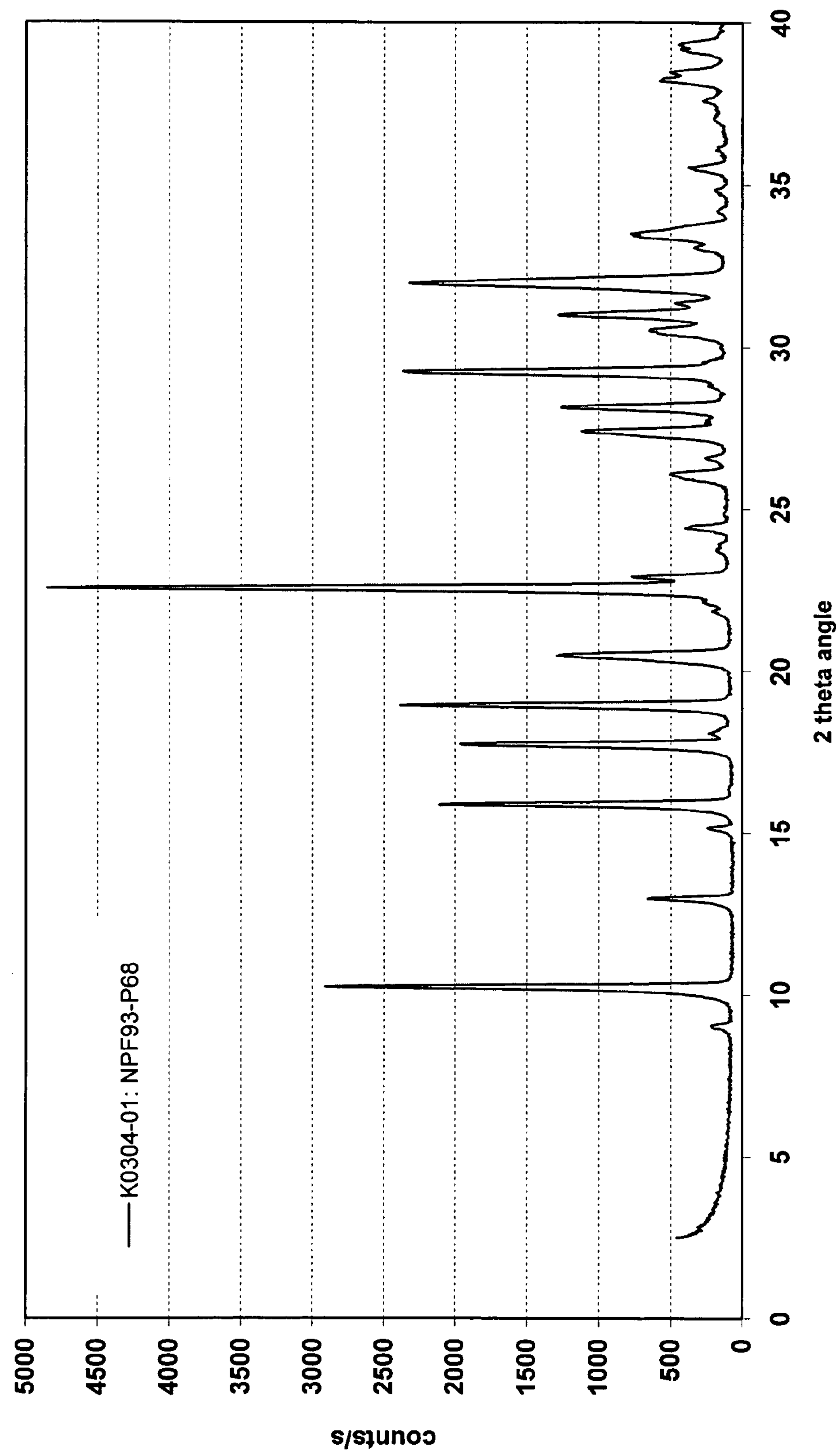
FIG. 4 is a characteristic X-ray powder diffraction pattern for form D
Figure 5:
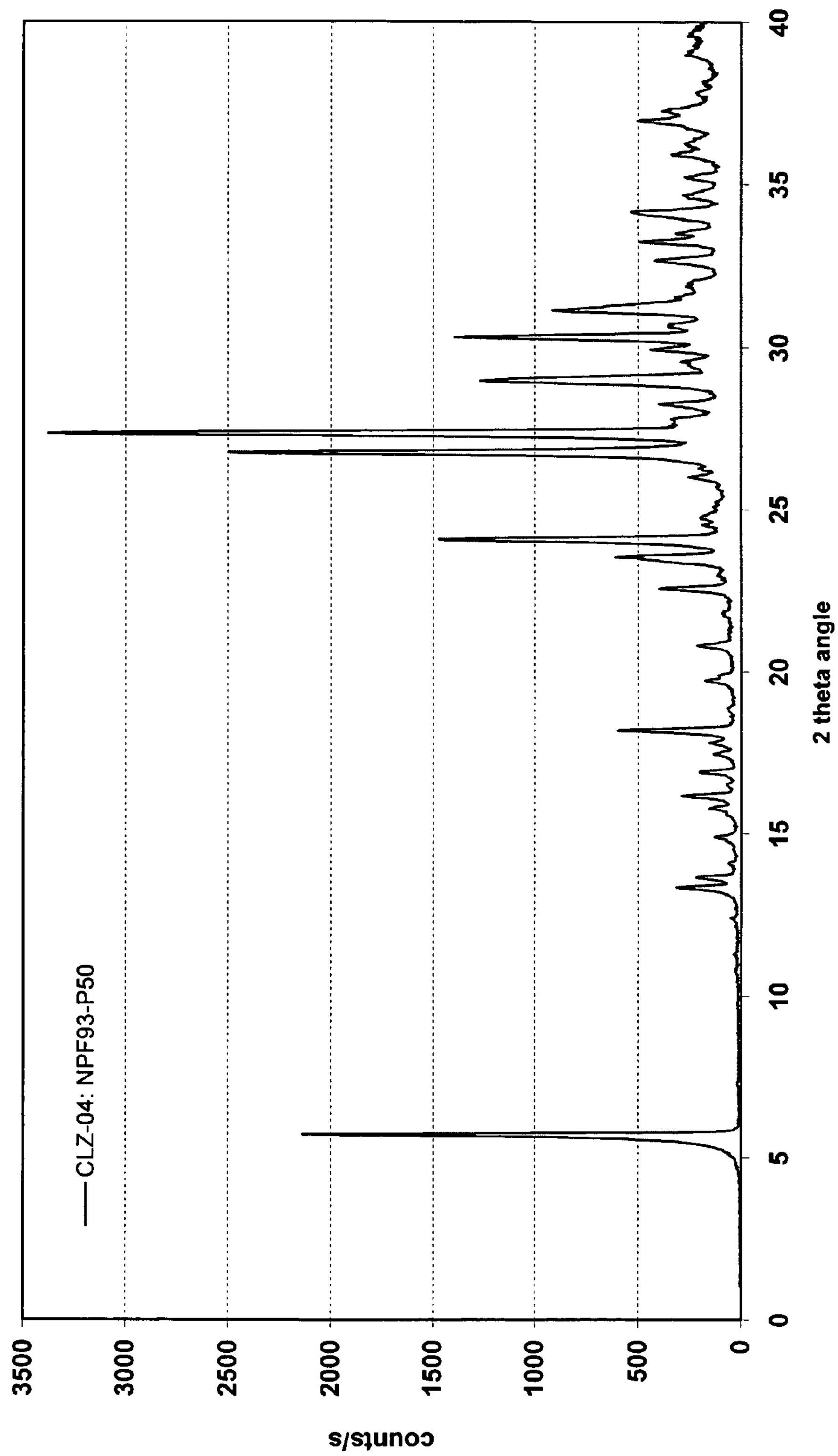
FIG. 5 is a characteristic X-ray powder diffraction pattern for form E
Figure 6:
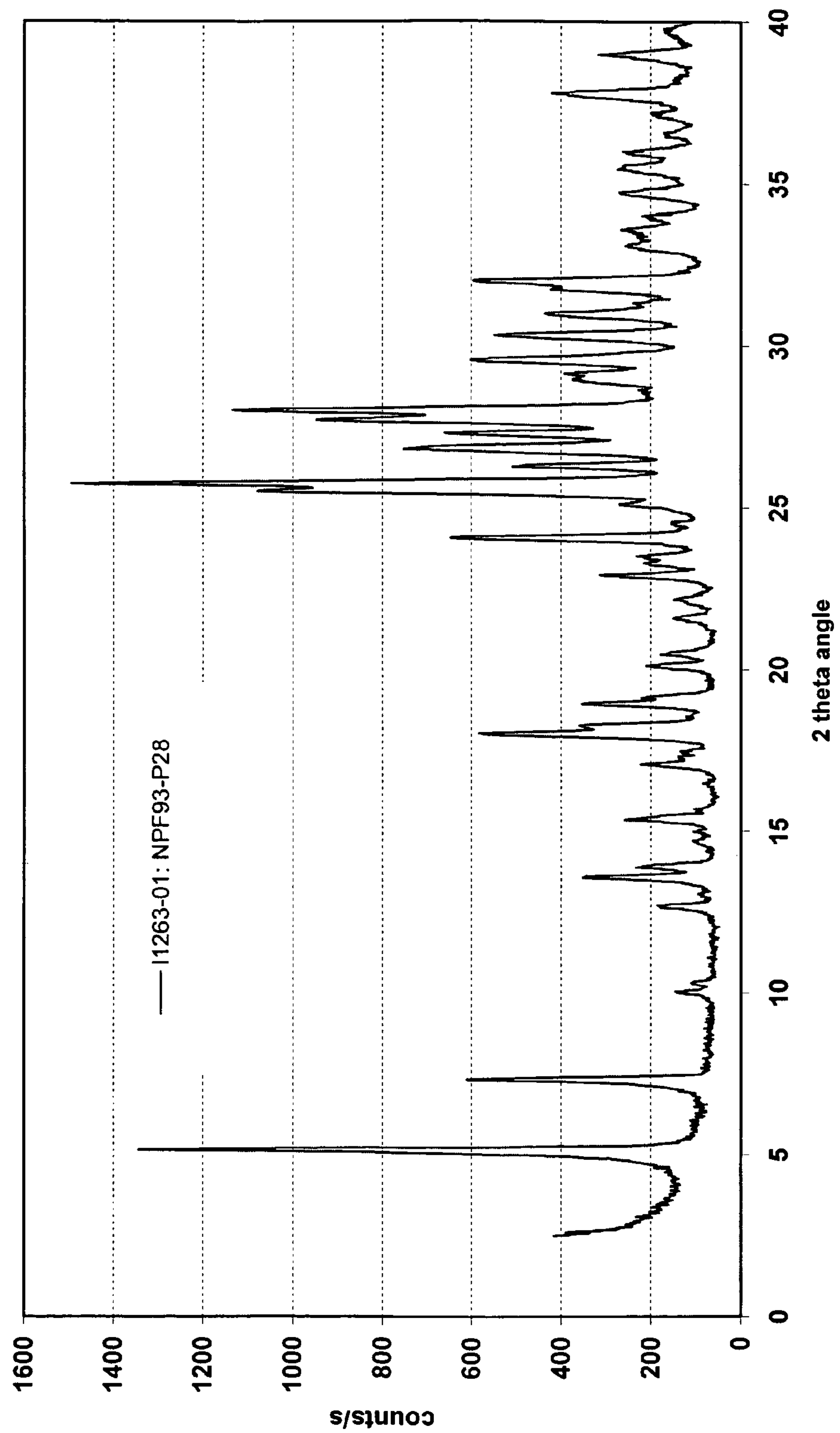
FIG. 6 is a characteristic X-ray powder diffraction pattern for form F
Figure 7:
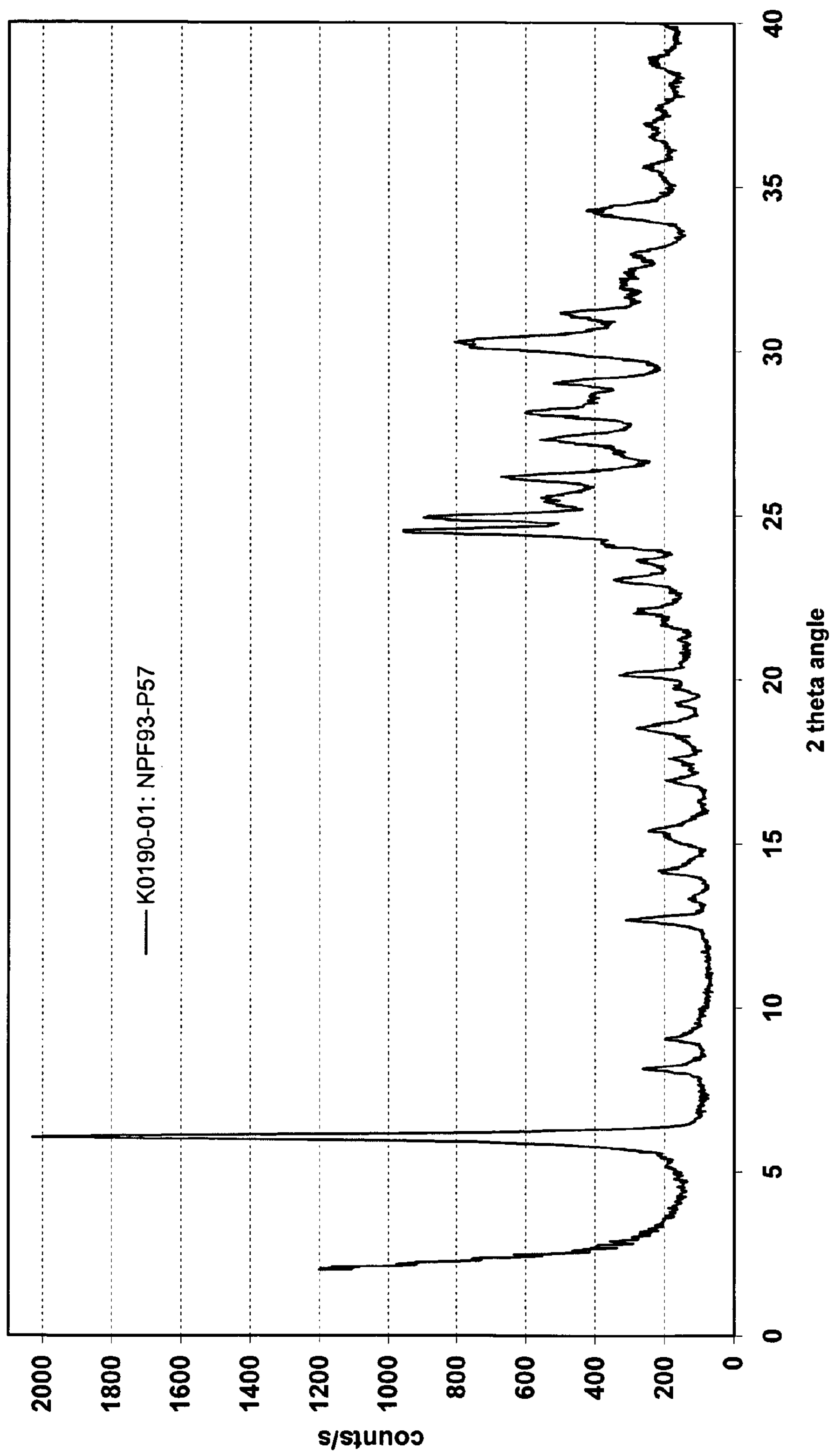
FIG. 7 is a characteristic X-ray powder diffraction pattern for form G
Figure 8:
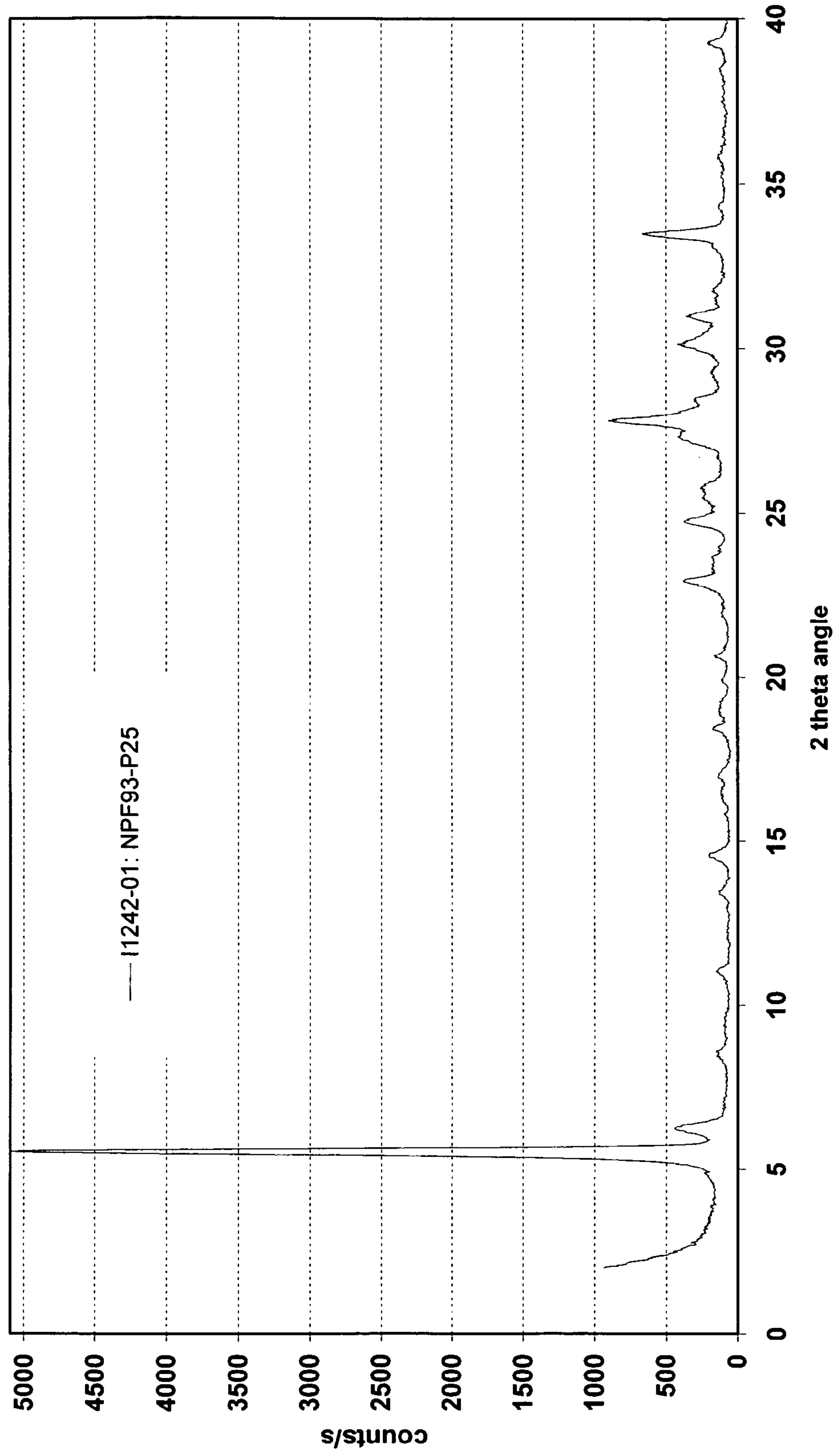
FIG. 8 is a characteristic X-ray powder diffraction pattern for form H
Figure 9:
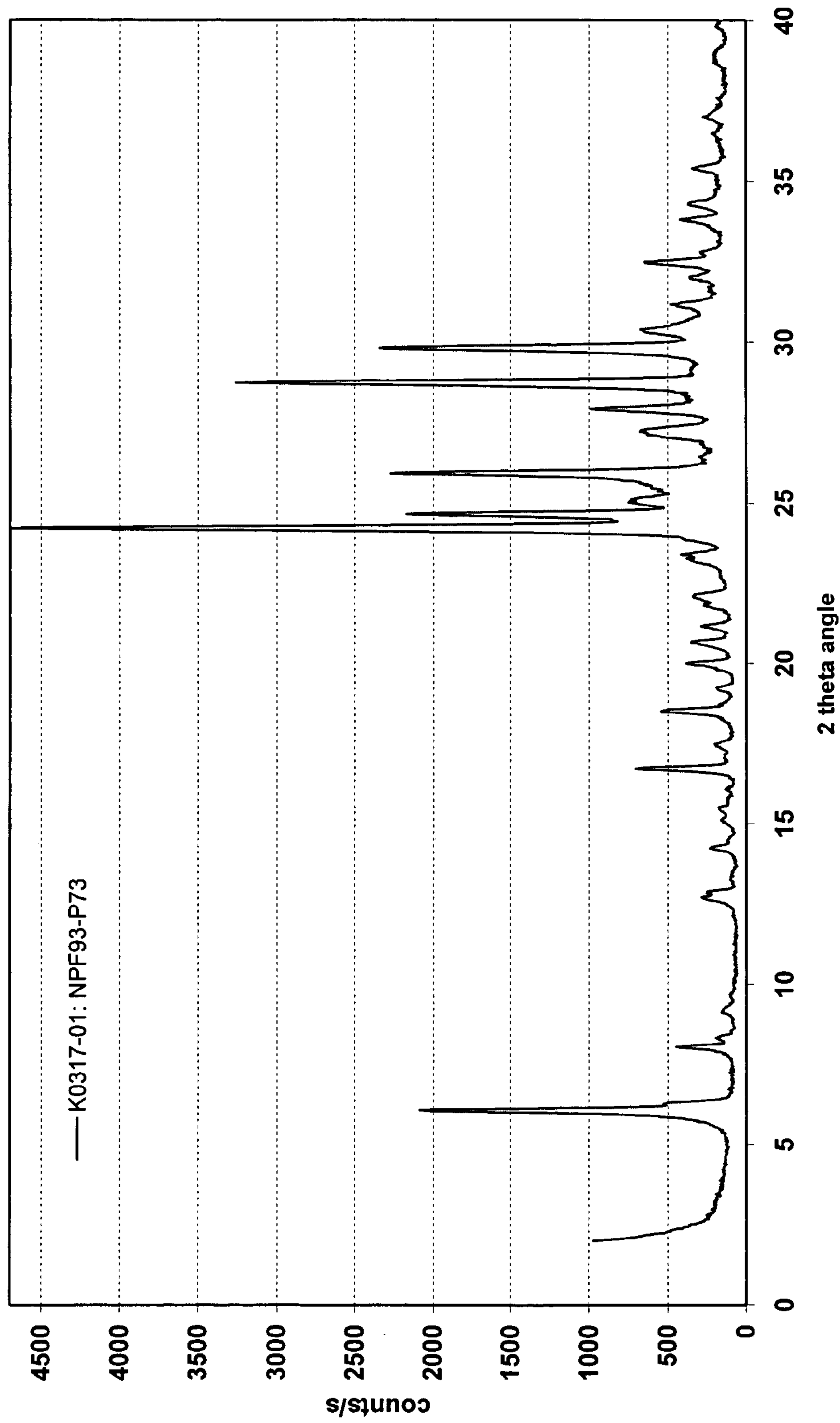
FIG. 9 is a characteristic X-ray powder diffraction pattern for form I
Figure 10:
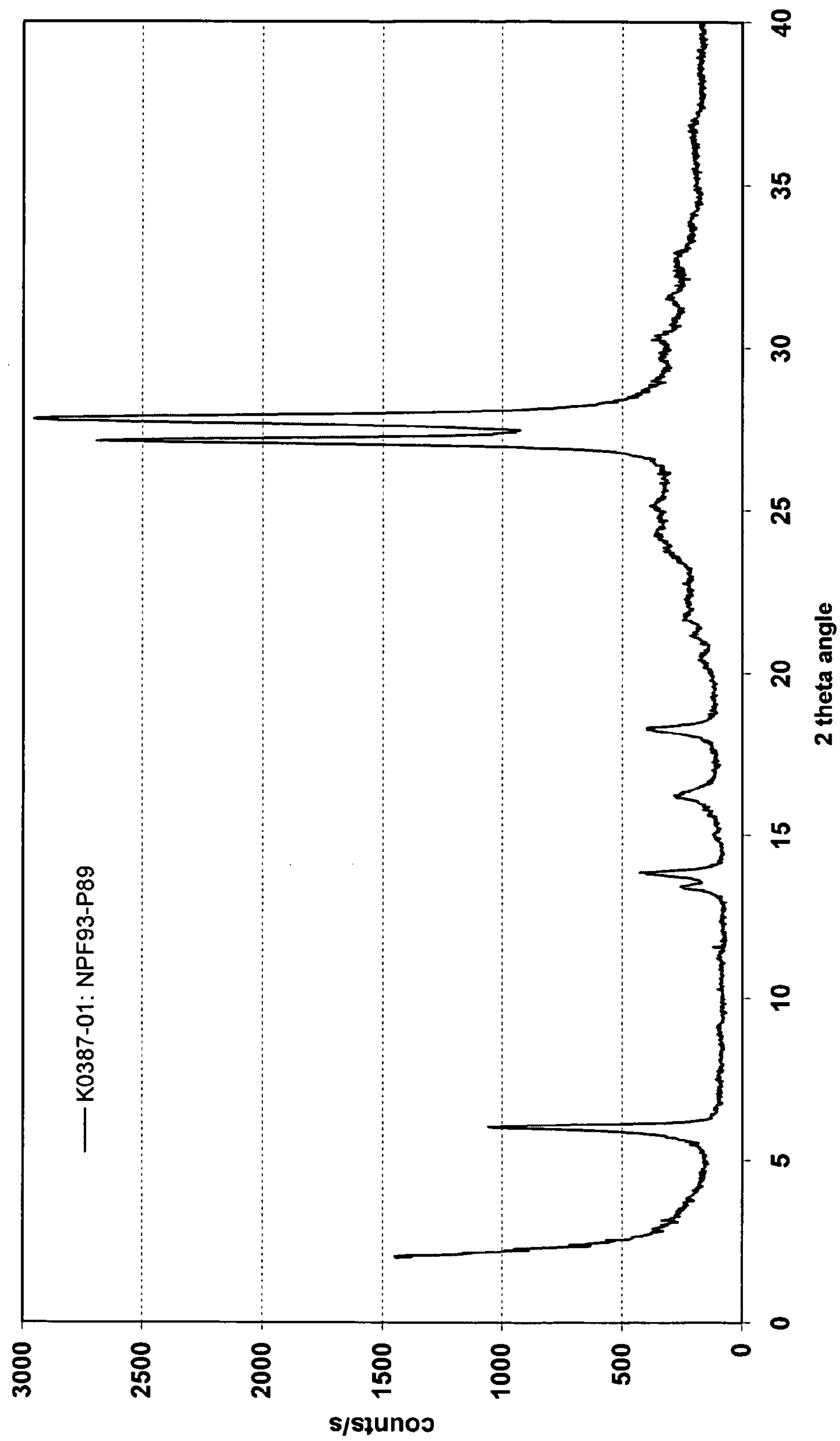
FIG. 10 is a characteristic X-ray powder diffraction pattern for form J
Figure 11:
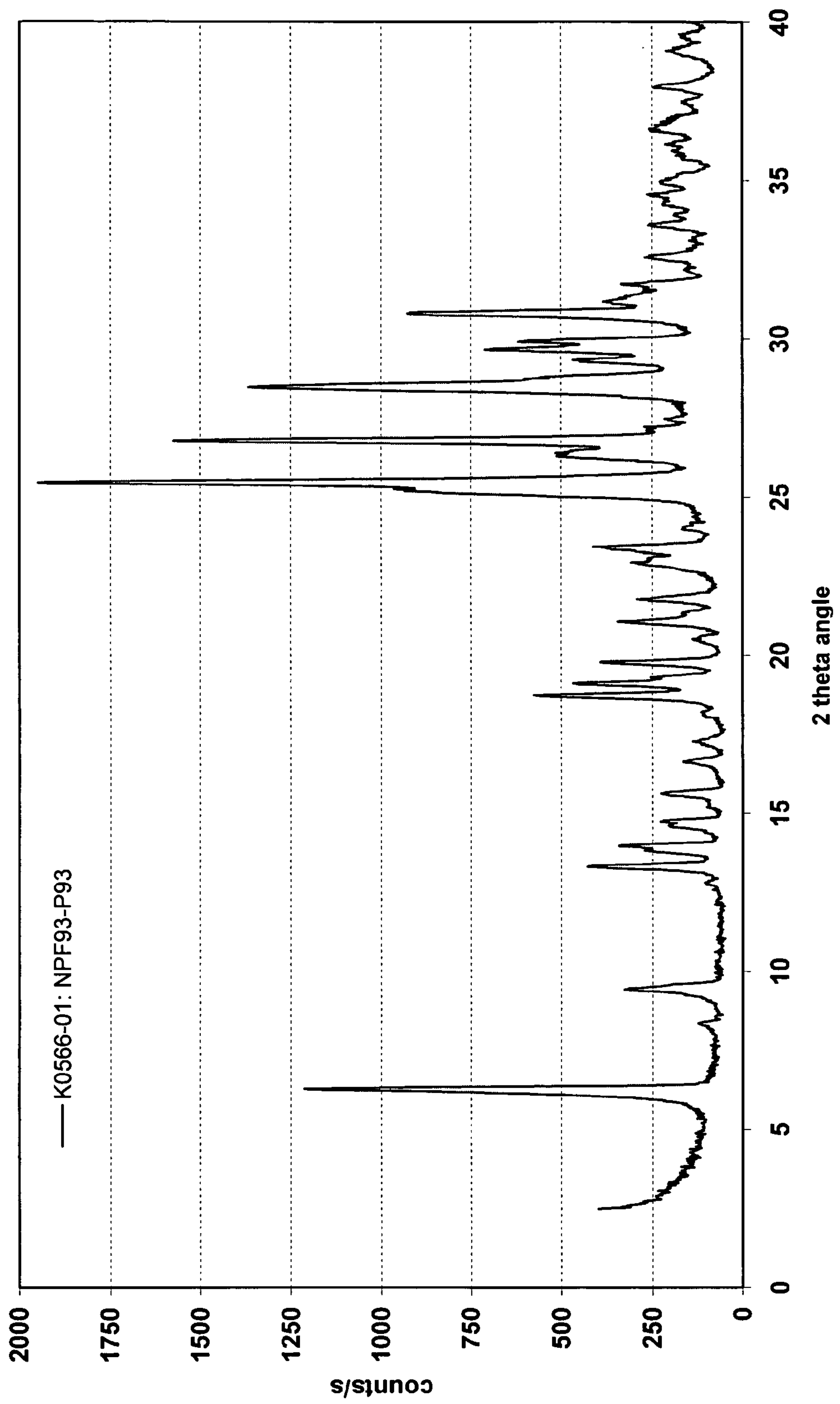
FIG. 11 is a characteristic X-ray powder diffraction pattern for form K
Figure 12:
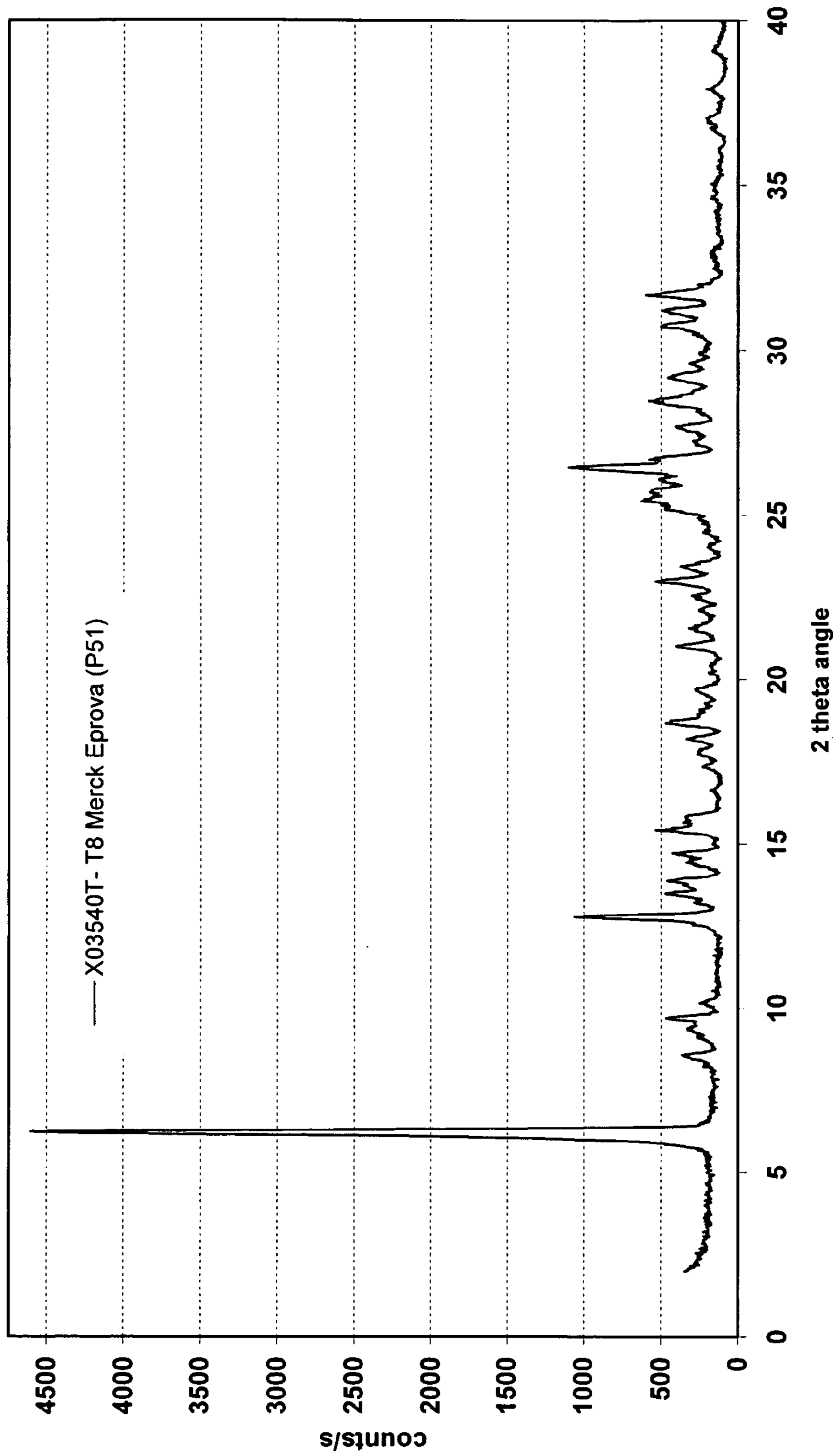
FIG. 12 is a characteristic X-ray powder diffraction pattern for form L
Figure 13:
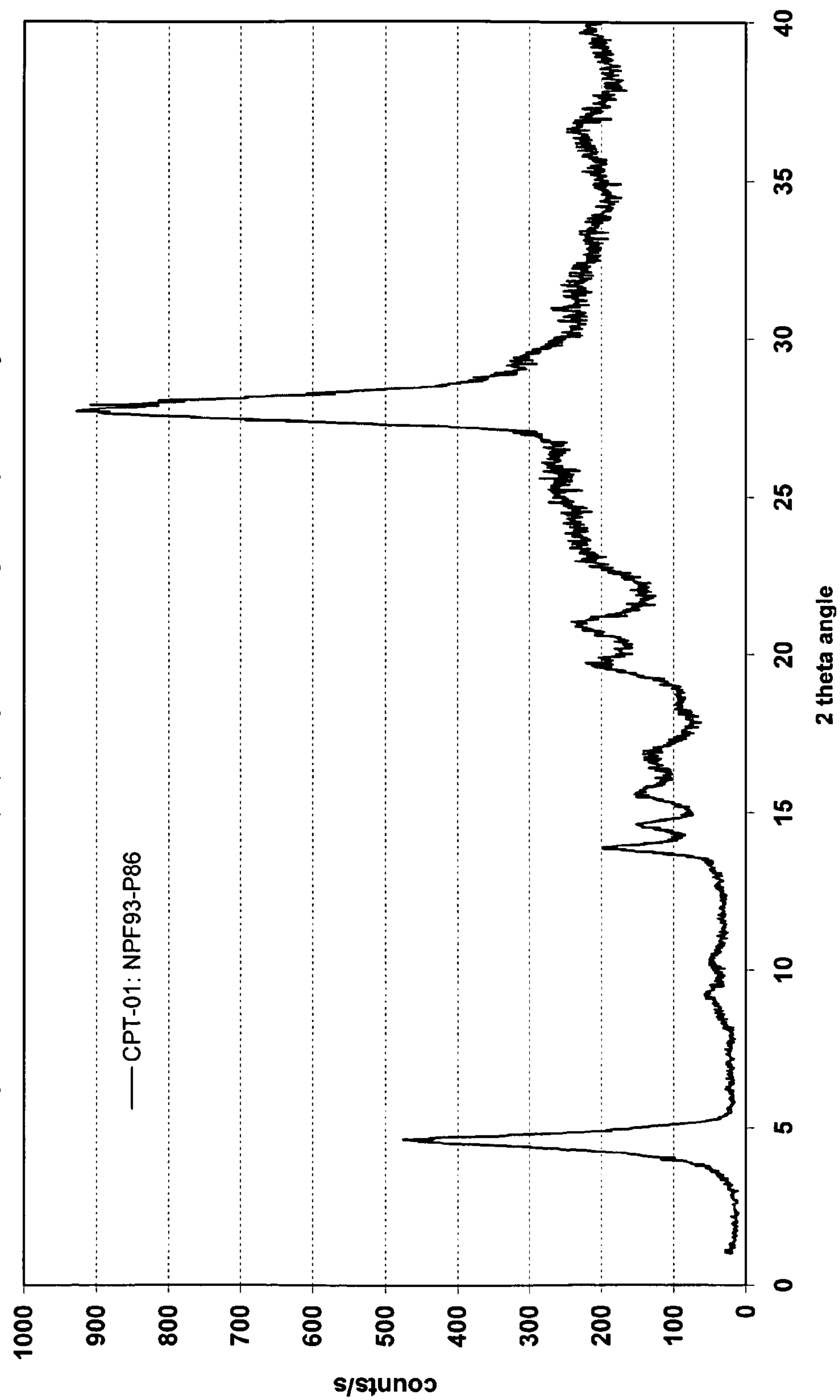
FIG. 13 is a characteristic X-ray powder diffraction pattern for form M
Figure 14:
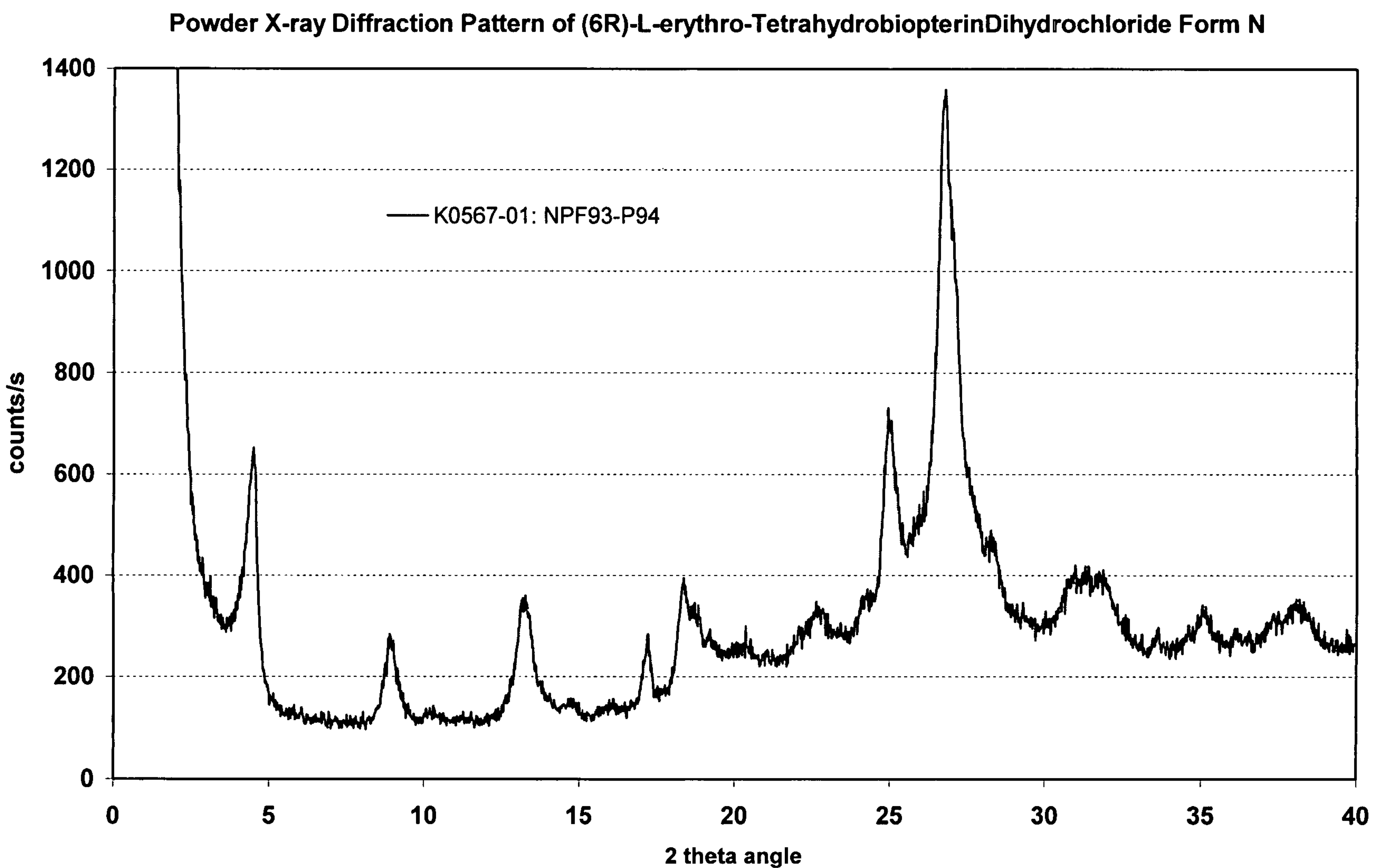
FIG. 14 is a characteristic X-ray powder diffraction pattern for form N
Figure 15:
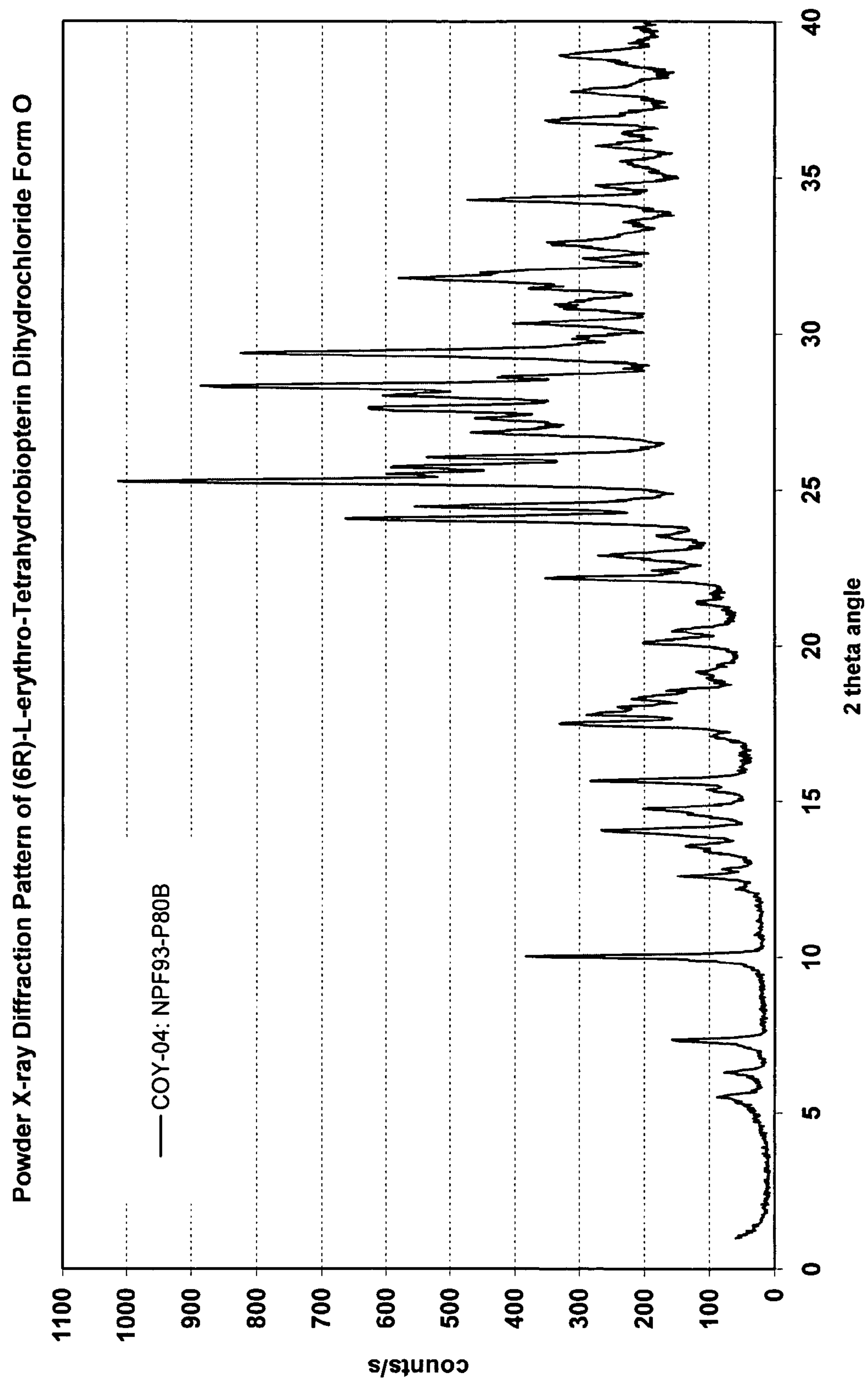
FIG. 15 is a characteristic X-ray powder diffraction pattern for form O

3. A crystalline form of (6R)-L-erythro-tetrahydrobiopterin dihydrochloride, which exhibits a characteristic X-ray powder diffraction pattern for form A as exhibited in FIG. 1; or
for form F as exhibited in FIG. 6; or
for form J as exhibited in FIG. 10; or
for form K as exhibited in FIG. 11; or
for form C as exhibited in FIG. 3; or
for form D as exhibited in FIG. 4; or
for form E as exhibited in FIG. 5; or
for form H as exhibited in FIG. 8; or
for form O as exhibited in FIG. 15; or
for form G as exhibited in FIG. 7; or
for form I as exhibited in FIG. 9; or
for form L as exhibited in FIG. 12; or
for form M as exhibited in FIG. 13; or
for form N as exhibited in FIG. 14.

4. A pharmaceutical composition comprising a purified crystalline form of (6R)-L-erythro-tetrahydrobiopterin dihydrochloride according to claim 1 of at least about 98% purity by high performance liquid chromatography or a combination of more than one of the purified crystalline forms, and a pharmaceutically acceptable carrier, diluent, excipient or adjuvant.

5. A pharmaceutical composition according to claim 4, further comprising folate, alone or together with arginine.

6. A pharmaceutical composition according to claim 5, wherein the folate is folic acid or a tetrahydrofolate selected from tetrahydrofolic acid, 5,10-methylenetetrahydrofolic acid, 10-formyltetrahydrofolic acid, 5-formyltetrahydrofolic acid or 5-methyltetrahydrofolic acid, or a polyglutamate thereof or a pharmaceutically acceptable salt thereof.

7. A pharmaceutical composition according to claim 5, wherein the folate is present as an optically pure diastereoisomer, a mixture of diastereoisomers, or a racemic mixture, and/or the pharmaceutically acceptable salt is a salt of sodium, potassium, calcium or ammonium.

8. A pharmaceutical composition according to claim 4, wherein the crystalline form of (6R)-L-erythro-tetrahydrobiopterin dihydrochloride is of at least about 98% purity by high performance liquid chromatography.

Figure 2:
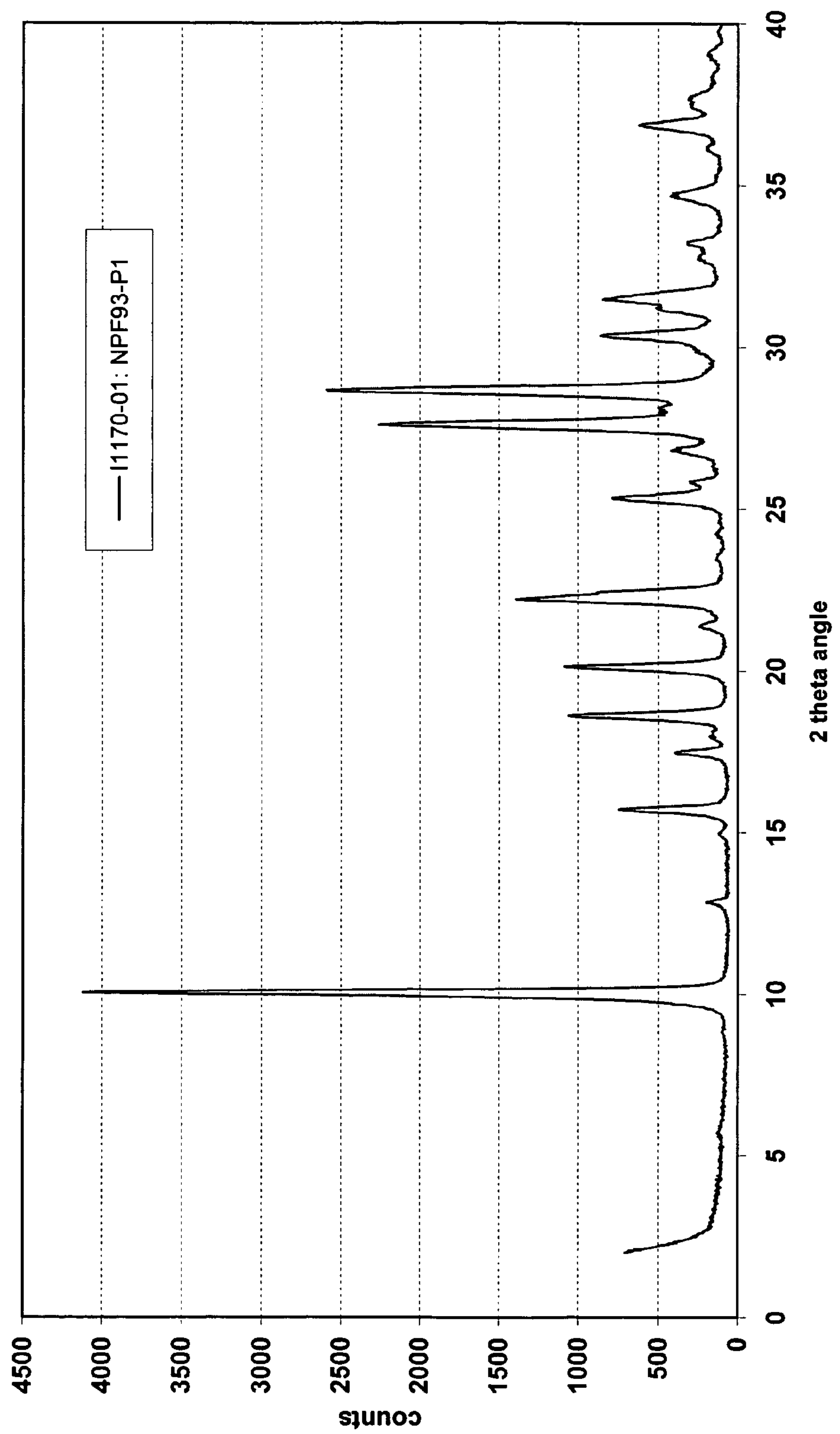
FIG. 2 is a characteristic X-ray powder diffraction pattern for form B

9. A pharmaceutical tablet comprising a purified crystalline polymorph of (6R)-L-erythro-tetrahydrobiopterin dihydrochloride, form B, which exhibits a characteristic X-ray powder diffraction pattern with the following characteristic peaks expressed in d-values (Å): 8.7 (vs), 5.63 (m), 4.76 (m), 4.40 (m), 4.00 (s), 3.23 (s), 3.11 (vs); or which exhibits a characteristic X-ray powder diffraction pattern as exhibited in FIG. 2; and polyvinylpyrrolidone as a biologically degradable polymeric binder and dicalcium phosphate as an excipient.

10. A pharmaceutical tablet comprising a purified crystalline polymorph of (6R)-L-erythro-tetrahydrobiopterin dihydrochloride, form B, which exhibits a characteristic X-ray powder diffraction pattern with the following characteristic peaks expressed in d-values (Å): 8.7 (vs), 6.9 (w), 5.90 (vw), 5.63 (m), 5.07 (m), 4.76 (m), 4.40 (m), 4.15 (w), 4.00 (s), 3.95 (m), 3.52 (m), 3.44 (w), 3.32 (m), 3.23 (s), 3.17 (w), 3.11 (vs), 3.06 (w), 2.99 (w), 2.96 (w), 2.94 (m), 2.87 (w), 2.84 (s), 2.82 (m), 2.69 (w), 2.59 (w), and 2.44 (w); and polyvinylpyrrolidone as a biologically degradable polymeric binder and dicalcium phosphate as an excipient.

11. A pharmaceutical tablet comprising a purified crystalline polymorph of (6R)-L-erythro-tetrahydrobiopterin dihydrochloride, form B, which exhibits a characteristic X-ray powder diffraction pattern as exhibited in FIG. 2; and polyvinylpyrrolidone as a biologically degradable polymeric binder and dicalcium phosphate as an excipient.

12. A pharmaceutical tablet comprising only one active ingredient, wherein said active ingredient consists essentially of purified crystalline polymorph of (6R)-L-erythro-tetrahydrobiopterin dihydrochloride, form B, which exhibits a characteristic X-ray powder diffraction pattern with the following characteristic peaks expressed in d-values (Å): 8.7 (vs), 5.63 (m), 4.76 (m), 4.40 (m), 4.00 (s), 3.23 (s), 3.11 (vs); or which exhibits a characteristic X-ray powder diffraction pattern with the following characteristic peaks expressed in d-values (Å): 8.7 (vs), 6.9 (w), 5.90 (vw), 5.63 (m), 5.07 (m), 4.76 (m), 4.40 (m), 4.15 (w), 4.00 (s), 3.95 (m), 3.52 (m), 3.44 (w), 3.32 (m), 3.23 (s), 3.17 (w), 3.11 (vs), 3.06 (w), 2.99 (w), 2.96 (w), 2.94 (m), 2.87 (w), 2.84 (s), 2.82 (m), 2.69 (w), 2.59 (w), and 2.44 (w); or which exhibits a characteristic X-ray powder diffraction pattern as exhibited in FIG. 2;

and polyvinylpyrrolidone as a biologically degradable polymeric binder and dicalcium phosphate as an excipient.

13. A pharmaceutical tablet according to claim 12, wherein the purified crystalline polymorph of (6R)-L-erythro-tetrahydrobiopterin dihydrochloride is of at least about 98% purity by high performance liquid chromatography.

14. A process for preparing a pharmaceutical tablet according to claim 9 comprising (a) providing a purified crystalline polymorph of form B of (6R)-L-erythro-tetrahydrobiopterin dihydrochloride of at least about 98% purity by high performance liquid chromatography, and (b) mixing the purified crystalline polymorph with polyvinylpyrrolidone and dicalcium phosphate.

15. A pharmaceutical tablet prepared by the process of claim 14.

16. A pharmaceutical tablet according to claim 9, further comprising folate alone or together with arginine.

17. A pharmaceutical tablet according to claim 9, further comprising a lubricant, a vitamin and a sugar.

18. A pharmaceutical tablet according to claim 10, further comprising a lubricant, a vitamin and a sugar.

19. A pharmaceutical tablet according to claim 11, further comprising a lubricant, a vitamin and a sugar.

20. A pharmaceutical tablet according to claim 12, further comprising a lubricant, a vitamin and a sugar.

* * * * *